(12) United States Patent
Takeuchi et al.

(10) Patent No.: US 6,780,616 B1
(45) Date of Patent: Aug. 24, 2004

(54) ANTIBIOTIC CAPRAZAMYCINS AND PROCESS FOR PRODUCING THE SAME

(75) Inventors: Tomio Takeuchi, Tokyo (JP); Masayuki Igarashi, Atsugi (JP); Hiroshi Naganawa, Tokyo (JP); Masa Hamada, Tokyo (JP)

(73) Assignees: Zaidan Hojin Biseibutsu Kagaku Kenkyu Kai Corp., Tokyo (JP); Meiji Seika Kaisa, Ltd., Tokyo (JP)

( * ) Notice: Subject to any disclaimer, the term of this patent is extended or adjusted under 35 U.S.C. 154(b) by 45 days.

(21) Appl. No.: 10/049,970

(22) PCT Filed: Aug. 11, 2000

(86) PCT No.: PCT/JP00/05415

§ 371 (c)(1),
(2), (4) Date: May 9, 2002

(87) PCT Pub. No.: WO01/12643

PCT Pub. Date: Feb. 22, 2001

(30) Foreign Application Priority Data

Aug. 12, 1999 (JP) ............................................. 11-228866

(51) Int. Cl.[7] ........................ A61K 31/70; C07H 17/00; C12P 19/44; C12N 1/00
(52) U.S. Cl. ........................ 435/74; 435/85; 435/886; 514/25; 514/42; 536/4.1; 536/17.4; 536/22.1
(58) Field of Search ................... 435/74, 85, 886; 514/25, 42; 536/4.1, 17.4, 22.1

(56) References Cited

U.S. PATENT DOCUMENTS 4,699,879 A * 10/1987 Umezawa et al. .......... 435/116

FOREIGN PATENT DOCUMENTS

| JP | 2-306992 | 12/1990 |
|----|----------|---------|
| WO | 97/41248 | 6/1997 |

OTHER PUBLICATIONS

Ubutaka, M. et al., "Structure Elucidation of Liposidomycins, a Class of Complex Lipid Nucleotide Antibiotics", J. Org. Chem (Nov. 20, 1992) vol. 57, No. 24, pp. 6392–6403.
Knapp, S. et al., "Synthesis of the Liposidomycin Diazepanone", Tetrahedron Lett. (Sep. 15, 1992) vol. 33, No. 38, pp. 5485–5486.
Kimura, K. et al., "Liposidmycin C Inhibits Phospho- -N-acetylmuramyl-pentapeptide transferase in Peptidoglycan Synthesis of *Escherichia coli* Y10", Argi. Biol. Chem. (Aug. 1, 1989) vol. 53, No. 7, pp. 1811–1815.
M. Ubukata, "Shinki Kousei Busshitsu no Kagakuteki Kenkyuu", Journal of Japan Society for Bioscience, Biotechnology and Agrochemistry (JSBA), vol. 62, No. 11, Nov., 1988 (Tokyo) pp. 1629–1636.
Ubutaka, M. et al. "The Structure of Liposidomycin B, an Inhibitor of Bacterial Petidoglycan Synthesis.", J. Am. Chem. Soc. (Jun. 22, 1988) vol. 110, No. 13, pp. 4416–4417.

* cited by examiner

*Primary Examiner*—Elli Peselev
(74) *Attorney, Agent, or Firm*—Abelman, Frayne & Schwab

(57) ABSTRACT

There have been obtained, by cultivation of Streptomyces sp. MK730-62F2 (deposit number of FERM BP-7218), antibiotic caprazamycins A to F having by the following general formula (I)

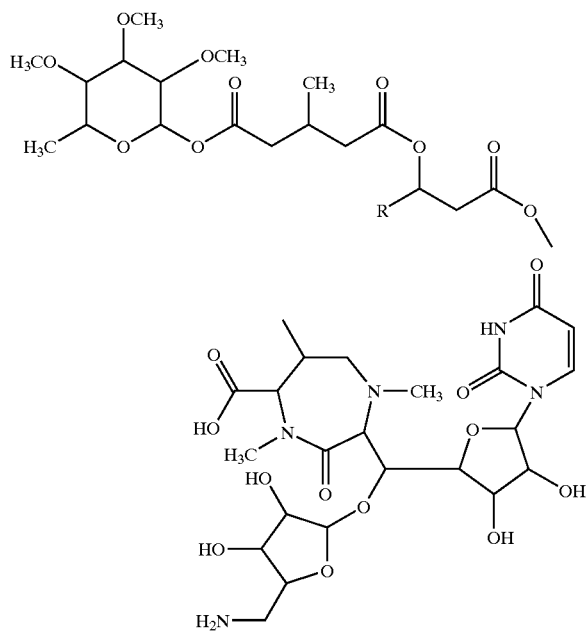

wherein R is tridecyl group, 11-methyl-dodecyl group, and others. These caprazamycins have excellent antibacterial activities against various acid-fast bacteria and various bacteria as well as their drug-resistant strains.

10 Claims, 20 Drawing Sheets

ANTIBIOTIC CAPRAZAMYCINS AND PROCESS FOR PRODUCING THE SAME

This application is filed under 35 USC §371 and priority is based on PCT/JP00/05415.

TECHNICAL FIELD

This invention relates to new antibiotics, namely caprazamycins A, B, C, E and F or pharmaceutically acceptable salts thereof, which have excellent antibacterial activities. This invention also relates to a process for producing a caprazamycin. Further, this invention relates to a pharmaceutical composition, particularly an antibacterial composition, comprising a caprazamycin or a salt thereof as an active ingredient. Still further, this invention relates to Streptomyces sp. MK730-62F2, as a new microorganism, having a characteristic nature that it is capable of producing a caprazamycin.

BACKGROUND ART

In chemotherapy of bacterial infections, particularly chemotherapy of infections of acid-fast bacteria, there have hitherto been used rifampicin, kanamycin, streptomycin, viomycin, capreomycin, cycloserine and the like, as antibacterial drug.

A serious problem for the chemotherapy of the bacterial infections is in that bacteria causative for the bacterial infections become drug-resistant. In particular, the appearance of acid-fast bacteria which are resistant to rifampicin, kanamycin, streptomycin, viomycin, capreomycin cycloserine and the like has brought about a social problem in respect of the chemotherapy of these bacterial infections. Thus, there is now a keen request for providing a novel chemotherapeutic agent which is effective against the bacterial infections as induced by the acid-fast bacteria resistant to antibacterial drug. Strongly requested also is a novel chemotherapeutic drug effective against the bacterial infections which are induced by atypical acid-fast bacteria and for which no chemotherapeutic treatment has been established yet. In order to meet these requisites, therefore, there exists a strong demand to find out or to create novel compounds which have novel chemical structure and can exhibit good properties such as excellent antibacterial activities in a different way from those of the known antibiotics as hitherto utilized. The object of this invention is therefore to provide novel antibiotics which have excellent antibacterial activities and are capable of meeting the requisites as above-mentioned.

DISCLOSURE OF THE INVENTION

We, the inventors of this invention, have carried out our investigations with the intention of finding out useful antibiotics. As a result, we have now found that a new microbial strain which belongs to genus Streptomyce and has been isolated by us can produce plural antibiotics having a novel skeletal structure. We have now designated a class of these plural antibiotics, collectively, as a caprazamycin. We have further found that a caprazamycin exhibits strong antibacterial activities against a variety of acid-fast bacteria and gram-positive bacteria as well as their drug-resistant strains. We have further proceeded our studies and have now found from the analysis of the caprazamycins, that the caprazamycins as now obtained by us include five compounds. We have designated these five compounds as caprazamycins A, B, C, E and F, respectively, and have decided their chemical structures. Furthermore, we have now found and confirmed that caprazamycins A, B, C, E and F are novel compounds and that they are collectively represented by a general formula (I) given below. By the way, these caprazamycins have a common and basic skeletal structure as shown in the general formula (I), wherein the side chain group R is a straight chain or branched chain alkyl group of 11 to 13 carbon atoms different from each other.

Deposit Information

The strain that is referred to herein as Streptomyces sp. MK730-62F2 was deposited on 27 Nov. 1998 under accession number FERM BP 7218 with the National Institute of Bioscience and Human Technology, Agency of Industrial Science and Technology, International Patent Organism Depository (IPOD) 1–3, Higashi 1-chome, Tsukuba-shi, Ibaraki-ken 305-8566 Japan, in accordance with the Budapest Treaty.

According to a first aspect of this invention, therefore, there is provided an antibiotic, caprazamycin A, caprazamycin B, caprazamycin C, caprazamycin E or caprazamycin F, which is a compound represented by the following general formula (I)

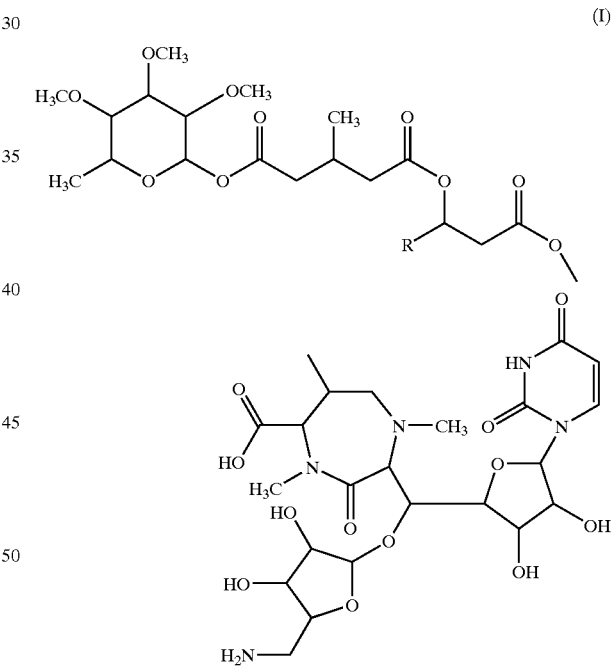

(I)

wherein R is tridecyl group for caprazamycin A; 11-methyl-dodecyl group for caprazamycin B; dodecyl group for caprazamycin C; undecyl group for caprazamycin E; and 9-methyl-decyl group for caprazamycin F, or a pharmaceutically acceptable salt thereof.

The novel antibiotic, a caprazamycin as now provided according to the first aspect of this invention includes caprazamycin A of formula (Ia), caprazamycin B of formula (Ib), caprazamycin C of formula (Ic), caprazamycin E of formula (Ie) and caprazamycin F of formula (If) as shown below.

(1) Caprazamycin A of the following formula (Ia)
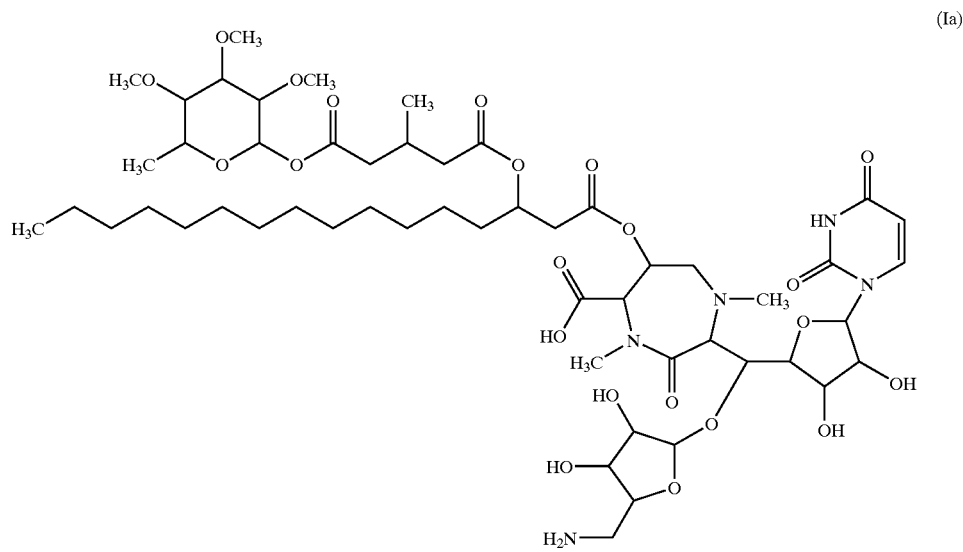
[Compound of general formula (I) where R is tridecyl group —(CH$_2$)$_{12}$—CH$_3$]
(2) Caprazamycin B of the following formula (Ib)
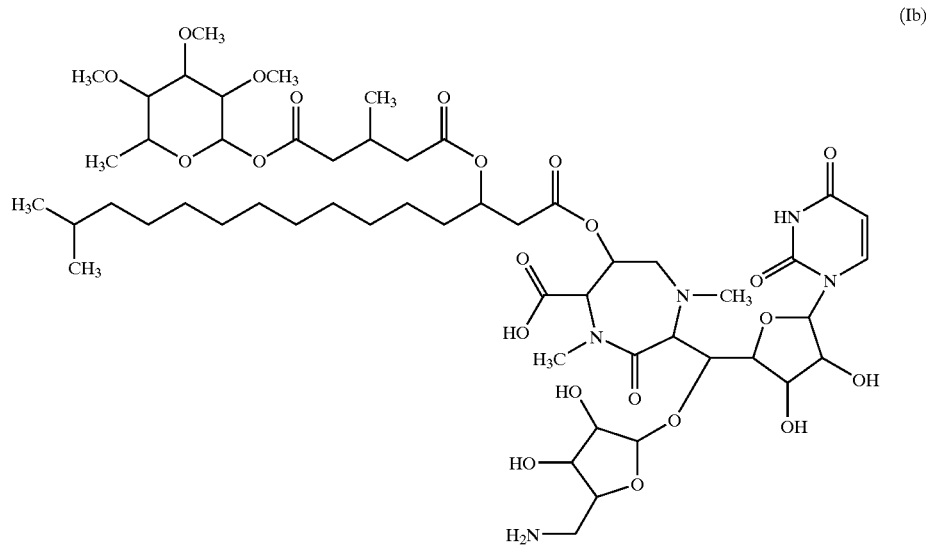
that is, compound of general formula (I) where R is 11-methyl-dodecyl group
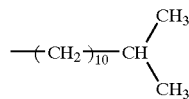

(3) Caprazamycin C of the following formula (Ic)
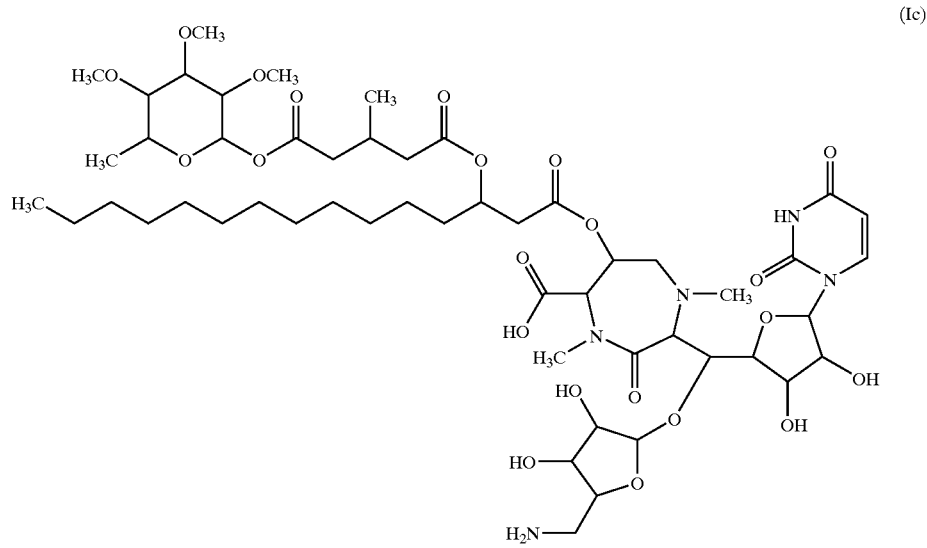
[Compound of general formula (I) where R is dodecyl group —(CH$_2$)$_{11}$—CH$_3$].
(4) Caprazamycin E of the following formula (Ie)
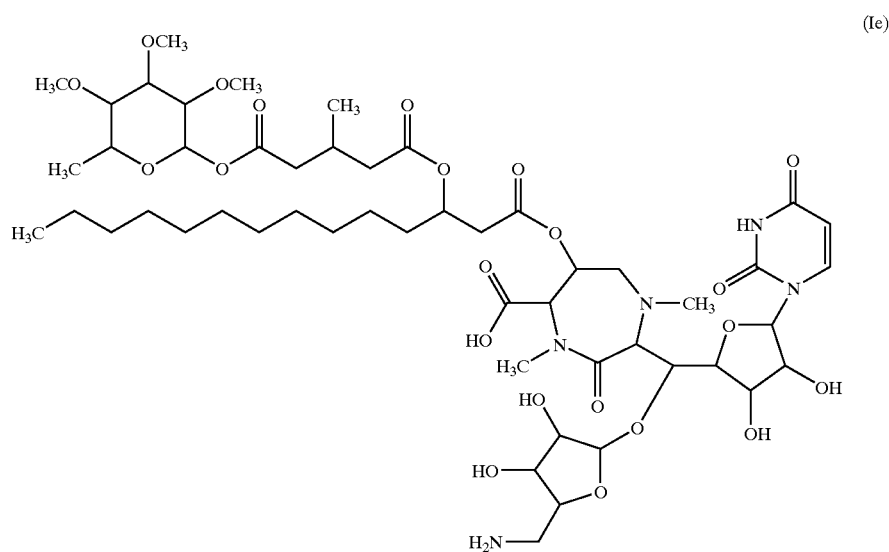

[Compound of general formula (I) where R is undecyl group —$(CH_2)_{10}$—$CH_3$], and
(5) Caprazamycin F of the following formula (If)

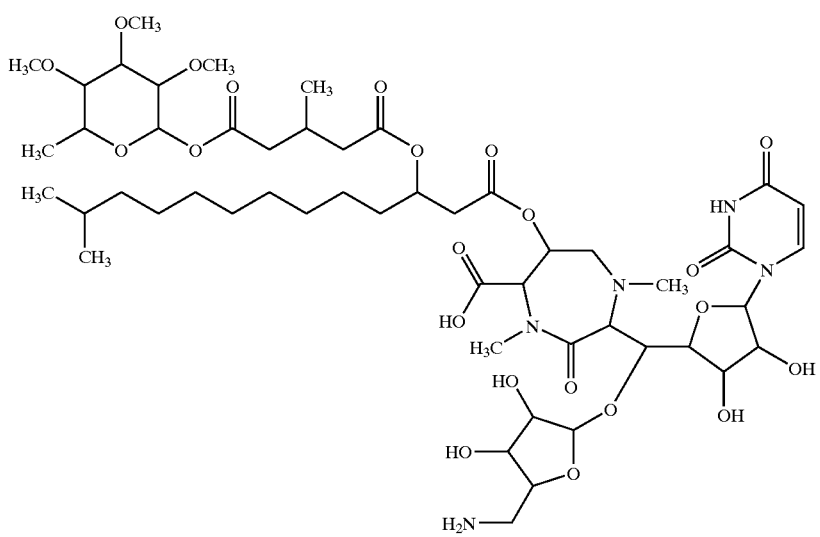

that is, a compound of general formula (I) where R is 9-methyl-decyl group

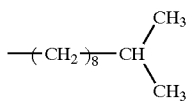

Physicochemical properties of caprazamycin A of formula (Ia) according to the first aspect of this invention are as follows.
(1) Appearance
Colorless powder
(2) Molecular formula

(3) High resolution mass spectrometry (HRFABMS: cation mode)
Found: 1146.5933 $(M+H)^+$
Calculated: 1146.5921
(4) Specific rotation
$[\alpha]_D^{23}$ −1.4° (c 0.83, DMSO)
(5) Ultraviolet absorption spectrum (in methanol)
$\lambda_{max}$ nm ($\epsilon$): 261 (7,400)
The UV spectrum is shown in FIG. 1 of attached drawings.
(6) Infrared absorption spectrum
As shown in FIG. 2 of attached drawings.
(7) Proton nuclear magnetic resonance spectrum
Proton NMR spectrum as measured in DMSO-$d_6$ at 500 MHz at room temperature is shown in FIG. 3 of attached drawings.
(8) $^{13}$C-nuclear magnetic resonance spectrum
$^{13}$C-NMR spectrum as measured in DMSO-$d_6$ at 125 MHz at room temperature is shown in FIG. 4 of attached drawings.
(9) Solubility
Soluble in methanol, dimethylsulfoxide (DMSO) and water, but insoluble in acetone and ethyl acetate.

(10) TLC
When it is subjected to a thin layer chromatography on silica gel 60$F_{254}$ (a product of Merck & Co.) as developed with a solvent consisting of butanol-methanol-water (4:1:2), the $R_f$ value is 0.44.

Caprazamycin A according to the first aspect of this invention is an amphoteric substance, and the pharmaceutically acceptable salts thereof may be exemplified by its salts with organic bases such as quaternary ammonium salts, its salts with various metals, for example, its salts with alkali metals such as sodium salt, or its acid addition salts with organic acids such as acetic acid or with inorganic acid such as hydrochloric acid.

Physicochemical properties of caprazamycin B of formula (Ib) according to the first aspect of this invention are as follows.
(1) Appearance
Colorless powder
(2) Molecular formula

(3) High resolution mass spectrometry (HRFABMS: anion mode)
Found: 1144.5750 $(M-H)^-$
Calculated: 1144.5764
(4) Specific rotation
$[\alpha]_D^{23}$ −2.60° (c 0.91, DMSO)
(5) Ultraviolet absorption spectrum (in methanol)
$\lambda_{max}$ nm ($\epsilon$): 261 (8,000)
The UV spectrum is shown in FIG. 5 of attached drawings.
(6) Infrared absorption spectrum
As shown in FIG. 6 of attached drawings.
(7) Proton nuclear magnetic resonance spectrum
Proton NMR spectrum as measured in a solvent mixture of DMSO-$d_6$-$D_2O$ (10:1) at 500 MHz at room temperature is shown in FIG. 7 of attached drawings.
(8) $^{13}$C-nuclear magnetic resonance spectrum
$^{13}$C-NMR spectrum as measured in a solvent mixture of DMSO-$d_6$-$D_2O$ (10:1) at 125 MHz at room temperature is shown in FIG. 8 of attached drawings.

(9) Solubility

Soluble in methanol, DMSO and water, but insoluble in acetone and ethyl acetate.

(10) TLC

When it is subjected to a thin layer chromatography on silica gel 60F$_{254}$ (a product of Merck & Co.) as developed with a solvent consisting of butanol-methanol-water (4:1:2), the R$_f$ value is 0.44.

Caprazamycin B according to the first aspect of this invention is an amphoteric substance, and the pharmaceutically acceptable salts thereof may be exemplified by its salts with organic bases such as quaternary ammonium salts, its salts with various metals, for example, its salts with alkali metals such as sodium salt, or its acid addition salts with organic acids such as acetic acid or with inorganic acid such as hydrochloric acid.

Physicochemical properties of caprazamycin C of formula (Ic) according to the first aspect of this invention are as follows.

(1) Appearance

Colorless powder (2) Molecular formula

$C_{52}H_{85}N_5O_{22}$ (3) High resolution mass spectrometry (HRFABMS: cation mode)

Found: 1132.5747 (M+H)$^+$

Calculated: 1132.5764

(4) Specific rotation $[\alpha]_D^{25}$ −1.1° (c 1.33, DMSO)

(5) Ultraviolet absorption spectrum (in methanol)

λmax nm (ε): 261 (8,300)

The UV spectrum is shown in FIG. 9 of attached drawings.

(6) Infrared absorption spectrum

As shown in FIG. 10 of attached drawings.

(7) Proton nuclear magnetic resonance spectrum

Proton NMR spectrum as measured in DMSO-d$_6$ at 500 MHz at room temperature is shown in FIG. 11 of attached drawings.

(8) $^{13}$C-nuclear magnetic resonance spectrum $^{13}$C-NMR spectrum as measured in DMSO-d$_6$ at 125 MHz at room temperature is shown in FIG. 12 of attached drawings.

(9) Solubility

Soluble in methanol, DMSO and water, but insoluble in acetone and ethyl acetate.

(10) TLC

When it is subjected to a thin layer chromatography on silica gel 60F$_{254}$ (a product of Merck & Co.) as developed with a solvent consisting of butanol-methanol-water (4:1:2), the R$_f$ value is 0.44.

Caprazamycin C according to the first aspect of this invention is an amphoteric substance, and the pharmaceutically acceptable salts thereof may be exemplified by its salts with organic bases such as quaternary ammonium salts, its salts with various metals, for example, its salts with alkali metals such as sodium salt, or its acid addition salts with organic acids such as acetic acid or with inorganic acid such as hydrochloric acid.

Physicochemical properties of caprazamycin E of formula (Ie) according to the first aspect of this invention are as follows.

(1) Appearance

Colorless powder (2) Molecular formula

$C_{51}H_{83}N_5O_{22}$ (3) High resolution mass spectrometry (HRFABMS: cation mode)

Found: 1118.5613 (M+H)$^+$

Calculated: 1118.5608

(4) Specific rotation $[\alpha]_D^{25}$ −5.1° (c 0.83, DMSO)

(5) Ultraviolet absorption spectrum (in methanol)

λ$_{max}$ nm (ε): 262 (7,700)

The UV spectrum is shown in FIG. 13 of attached drawings.

(6) Infrared absorption spectrum

As shown in FIG. 14 of attached drawings.

(7) Proton nuclear magnetic resonance spectrum

Proton NMR spectrum as measured in DMSO-d$_6$ at 500 MHz at room temperature is shown in FIG. 15 of attached drawings.

(8) $^{13}$C-nuclear magnetic resonance spectrum $^{13}$C-NMR spectrum as measured in DMSO-d$_6$ at 125 MHz at room temperature is shown in FIG. 16 of attached drawings.

(9) Solubility

Soluble in methanol, DMSO and water, but insoluble in acetone and ethyl acetate.

(10) TLC

When it is subjected to a thin layer chromatography on silica gel 60F$_{254}$ (a product of Merck & Co.) as developed with a solvent consisting of butanol-methanol-water (4:1:2), the R$_f$ value is 0.44.

Caprazamycin E according to the first aspect of this invention is an amphoteric substance, and the pharmaceutically acceptable salts thereof may be exemplified by its salts with organic bases such as quaternary ammonium salts, its salts with various metals, for example, its salts with alkali metals such as sodium salt, or its acid addition salts with organic acids such as acetic acid or with inorganic acid such as hydrochloric acid.

Physicochemical properties of caprazamycin F of formula (If) according to the first aspect of this invention are as follows.

(1) Appearance

Colorless powder (2) Molecular formula

$C_{51}H_{83}N_5O_{22}$ (3) High resolution mass spectrometry (HRFABMS: cation mode)

Found: 1118.5615 (M+H)$^+$

Calculated: 1118.5608

(4) Specific rotation $[\alpha]_D^{25}$ −4.7° (c 0.90, DMSO)

(5) Ultraviolet absorption spectrum (in methanol)

λ$_{max}$ nm (ε): 262 (7,600)

The UV spectrum is shown in FIG. 17 of attached drawings.

(6) Infrared absorption spectrum

As shown in FIG. 18 of attached drawings.

(7) Proton nuclear magnetic resonance spectrum

Proton NMR spectrum as measured in DMSO-d$_6$ at 500 MHz at room temperature is shown in FIG. 19 of attached drawings.

(8) $^{13}$C-nuclear magnetic resonance spectrum $^{13}$C-NMR spectrum as measured in DMSO-d$_6$ at 125 MHz at room temperature is shown in FIG. 20 of attached drawings.

(9) Solubility

Soluble in methanol, DMSO and water, but insoluble in acetone and ethyl acetate.

(10) TLC

When it is subjected to a thin layer chromatography on silica gel 60F$_{254}$ (a product of Merck & Co.) as developed with a solvent consisting of butanol-methanol-water (4:1:2), the R$_f$ value is 0.44.

Caprazamycin F according to the first aspect of this invention is an amphoteric substance, and the pharmaceutically acceptable salts thereof may be exemplified by its salts with organic bases such as quaternary ammonium salts, its salts with various metals, for example, its salts with alkali metals such as sodium salt, or its acid addition salts with organic acids such as acetic acid or with inorganic acid such as hydrochloric acid.

By the way, the expression "a caprazamycin" simply given in this description may sometime mean either any one of caprazamycin A, caprazamycin B, caprazamycin C, caprazamycin E and caprazamycin F, or a mixture of two or more or a mixture of all of them.

Caprazamycins having the general formula (I) above according to this invention have biological properties hereinafter given.

Thus, caprazamycin A, caprazamycin B, caprazamycin C, caprazamycin E and caprazamycin F each exhibit antibacterial activities against such bacteria which embrace acid-fast bacteria, including their drug-resistant strains, as well as gram-positive bacteria, including their drug-resistant strains (methicillin-resistant strains, and others). The antibacterial activities of a caprazamycin against these bacteria are tested by the following procedures.

Test Example 1

The antibacterial spectrum of caprazamycin A against a variety of microorganisms were measured on a 1% glycerin-supplemented nutrient agar medium by a serial dilution method according to the standard method as provided by Japanese Society of Chemotherapy. The test results are shown in Table 1.

TABLE 1

| Microorganisms tested | Caprazamycin A Minimum growth inhibitory concentration (μg/ml) |
|---|---|
| Mycobacterium smegmatis ATCC607 | 1.56 |
| Mycobacterium smegmatis ATCC607 PM-R (paromomycin-resistant) | 1.56 |
| Mycobacterium smegmatis ATCC607 VM-R (viomycin-resistant) | 0.78 |
| Mycobacterium smegmatis ATCC607 CPM-R (capreomycin-resistant) | 0.78 |
| Mycobacterium smegmatis ATCC607 ST-R (streptothricin-resistant) | 0.78 |
| Mycobacterium smegmatis ATCC607 KM-R (kanamycin-resistant) | 0.78 |
| Mycobacterium smegmatis ATCC607 SM-R (streptomycin-resistant) | 1.56 |
| Mycobacterium smegmatis ATCC607 RFP-R (rifampicin-resistant) | 0.78 |
| Mycobacterium phlei | 1.56 |
| Mycobacterium vaccae ATCC15483 | 0.2 |
| Mycobacterium fortuitum | 6.25 |

Test Example 2

The antibacterial spectrum of caprazamycin B against a variety of microorganisms were measured on a 1% glycerin-supplemented nutrient agar medium by a serial dilution method according to the standard method as provided by Japanese Society of Chemotherapy. The test results are shown in Table 2.

TABLE 2

| Microorganisms tested | Caprazamycin B Minimum growth inhibitory concentration (μg/ml) |
|---|---|
| Mycobacterium smegmatis ATCC607 | 3.13 |
| Mycobacterium smegmatis ATCC607 PM-R (paromomycin-resistant) | 1.56 |
| Mycobacterium smegmatis ATCC607 VM-R (viomycin-resistant) | 1.56 |
| Mycobacterium smegmatis ATCC607 CPM-R (capreomycin-resistant) | 1.56 |
| Mycobacterium smegmatis ATCC607 ST-R (streptothricin-resistant) | 1.56 |
| Mycobacterium smegmatis ATCC607 KM-R (kanamycin-resistant) | 1.56 |
| Mycobacterium smegmatis ATCC607 SM-R (streptomycin-resistant) | 3.13 |
| Mycobacterium smegmatis ATCC607 RFP-R (rifampicin-resistant) | 3.13 |
| Mycobacterium phlei | 3.13 |
| Mycobacterium vaccae ATCC15483 | 0.39 |
| Mycobacterium fortuitum | 50 |

Test Example 3

The antibacterial spectrum of caprazamycin B against a variety of microorganisms other than the microorganisms as specified in Table 2 were measured on Müller-Hinton agar medium by a serial dilution method according to the standard method as provided by Japanese Society of Chemotherapy. The test results are shown in Table 3.

TABLE 3

| Microorganisms tested | Caprazamycin B Minimum growth inhibitory concentration (μg/ml) |
|---|---|
| Staphylococcus aureus FDA209P | 1.56 |
| Staphylococcus aureus Smith | 3.13 |
| Staphylococcus aureus MS9610 (multiple drug-resistant) | 3.13 |
| Staphylococcus aureus No.5 (methicillin-resistant) | 3.13 |
| Staphylococcus aureus No.17 (methicillin-resistant) | 6.25 |
| Staphylococcus aureus MS16526 (methicillin-resistant) | 3.13 |
| Staphylococcus aureus TY-04282 (methicillin-resistant) | 6.25 |
| Micrococcus luteus FDA16 | 3.13 |
| Micrococcus luteus PCI1001 | 3.13 |
| Bacillus anthracis | 0.78 |
| Bacillus subtilis NRRL B-558 | 12.5 |
| Bacillus subtilis PCI1219 | 6.25 |
| Bacillus cereus ATCC10702 | 3.13 |
| Corynebacterium bovis 1810 | 3.13 |
| Escherichia coli NIHJ | 100 |

Test Example 4

The antibacterial spectrum of caprazamycin C against a variety of microorganisms were measured on a 1% glycerin-supplemented nutrient agar medium by a serial dilution method according to the standard method as provided by Japanese Society of Chemotherapy. The test results are shown in Table 4.

TABLE 4

| Microorganisms tested | Caprazamycin C Minimum growth inhibitory concentration (µg/ml) |
|---|---|
| *Mycobacterium smegmatis* ATCC607 | 1.56 |
| *Mycobacterium smegmatis* ATCC607 PM-R (paromomycin-resistant) | 1.56 |
| *Mycobacterium smegmatis* ATCC607 VM-R (viomycin-resistant) | 1.56 |
| *Mycobacterium smegmatis* ATCC607 CPM-R (capreomycin-resistant) | 1.56 |
| *Mycobacterium smegmatis* ATCC607 ST-R (streptothricin-resistant) | 1.56 |
| *Mycobacterium smegmatis* ATCC607 KM-R (kanamycin-resistant) | 0.78 |
| *Mycobacterium smegmatis* ATCC607 SM-R (streptomycin-resistant) | 1.56 |
| *Mycobacterium smegmatis* ATCC607 RFP-R (rifampicin-resistant) | 1.56 |
| *Mycobacterium phlei* | 1.56 |
| *Mycobacterium vaccae* ATCC15483 | 0.39 |
| *Mycobacterium fortuitum* | 12.5 |

Test Example 5

The antibacterial spectrum of caprazamycin E against a variety of microorganisms were measured on a 1% glycerin-supplemented nutrient agar medium by a serial dilution method according to the standard method as provided by Japanese Society of Chemotherapy. The test results are shown in Table 5.

TABLE 5

| Microorganisms tested | Caprazamycin E Minimum growth inhibitory concentration (µg/ml) |
|---|---|
| Mycobacterium smegmatis ATCC607 | 1.56 |
| Mycobacterium smegmatis ATCC607 PM-R (paromomycin-resistant) | 1.56 |
| Mycobacterium smegmatis ATCC607 VM-R (viomycin-resistant) | 0.39 |
| Mycobacterium smegmatis ATCC607 CPM-R (capreomycin-resistant) | 0.39 |
| Mycobacterium smegmatis ATCC607 ST-R (streptothricin-resistant) | 0.78 |
| Mycobacterium smegmatis ATCC607 KM-R (kanamycin-resistant) | 0.78 |
| Mycobacterium smegmatis ATCC607 SM-R (streptomycin-resistant) | 1.56 |
| Mycobacterium smegmatis ATCC607 RFP-R (rifampicin-resistant) | 0.78 |
| Mycobacterium phlei | 1.56 |
| Mycobacterium vaccae ATCC15483 | 0.39 |
| Mycobacterium fortuitum | 12.5 |

Test Example 6

The antibacterial spectrum of caprazamycin F against a variety of microorganisms were measured on a 1% glycerin-supplemented nutrient agar medium by a serial dilution method according to the standard method as provided by Japanese Society of Chemotherapy. The test results are shown in Table 6.

TABLE 6

| Microorganisms tested | Caprazamycin F Minimum growth inhibitory concentration (µg/ml) |
|---|---|
| *Mycobacterium smegmatis* ATCC607 | 1.56 |
| *Mycobacterium smegmatis* ATCC607 PM-R (paromomycin-resistant) | 0.78 |
| *Mycobacterium smegmatis* ATCC607 VM-R (viomycin-resistant) | 1.56 |
| *Mycobacterium smegmatis* ATCC607 CPM-R (capreomycin-resistant) | 0.78 |
| *Mycobacterium smegmatis* ATCC607 ST-R (streptothricin-resistant) | 0.78 |
| *Mycobacterium smegmatis* ATCC607 KM-R (kanamycin-resistant) | 0.78 |
| *Mycobacterium smegmatis* ATCC607 SM-R (streptomycin-resistant) | 1.56 |
| *Mycobacterium smegmatis* ATCC607 RFP-R (rifampicin-resistant) | 0.78 |
| *Mycobacterium phlei* | 1.56 |
| *Mycobacterium vaccae* ATCC15483 | 0.78 |
| *Mycobacterium fortuitum* | 12.5 |

Test Example 7

The antibacterial spectrum of each of caprazamycins A, B, C, E and F against *Mycobacterium tuberculosis*, and against atypical acid-fast bacteria, *Mycobacterium avium* kirchberg and *Mycobacterium intracellulare*, were measured in a Middlebrook 7H9 liquid medium by a serial dilution method. At the same time, antibacterial spectra of rifampicin (RMP) and isonicotinic acid hydrazide (INH) (as comparative drug) against the above-mentioned acid-fast bacteria were measured by the same serial dilution method. The results obtained are shown in the following Table 7.

TABLE 7

| | Minimum Inhibitory Concentration of Compound tested against Test Bacteria given below (µg/mg) | | |
|---|---|---|---|
| Compound tested | *Mycobacterium tuberculosis* H37Rv NIHJ-1633 | *Mycobacterium avium* kirchberg NIHJ-1605 | *Mycobacterium intracellulare* E-1 NIHJ-1618 |
| Caprazamycin A | 1.56 | <0.025 | 0.78 |
| Caprazamycin B | 1.56 | <0.025 | 0.78 |
| Caprazamycin C | 0.78 | <0.025 | 0.78 |
| Caprazamycin E | 0.78 | <0.025 | 0.78 |
| Caprazamycin F | 1.56 | 0.1 | 1.56 |
| RMP(Comparative) | 0.1 | 0.78 | 0.2 |
| INH(Comparative) | 0.05 | 25 | 0.78 |

Further, according to a second aspect of this invention, there is provided a process for the production of antibiotics, caprazamycin A, caprazamycin B, caprazamycin C, caprazamycin E and/or caprazamycin F having the general formula (I) given above, characterized in that the process comprises culturing a microbial strain which belongs to the genus Streptomyces and which is capable of producing at least one of caprazamycin A, caprazamycin B, caprazamycin C, caprazamycin E and caprazamycin F, and recovering at least one of caprazamycins A, B, C, E and F from the resulting culture.

The microorgnism or microbial strain, which is capable of producing the antibiotic, a caprazamycin, and is usable in the process according to the second aspect of this invention, may be any strain of those microorganisms which have an ability of producing the said antibiotics that possess the above-mentioned physicochemical properties and biological properties, and it can be chosen from a wide variety of microorganisms. Among such usable microorganisms, there may be quoted a strain of actinomycetes, to which a strain number MK730-62F2 is alloted and which was isolated from a soil sample of Oafu island, Hi., by our Institute of Microbial Chemistry in March of 1997, as one preferred concrete example of the microorganism which is capable of producing the antibiotics, caprazamycins.

The microbiological properties of the strain MK730-62F2 are now described below.

1. Morphology

The strain MK730-62F2 has branched substrate mycelia, from which extend relatively long aerial hyphae with the formation of 5- to 10-turned spirals at the tips of the aerial hyphae. Chain of the matured spores is in the form of a chain comprising 10 to 50 oval spores, and the dimensions of the spores are about 0.5 to 0.6×0.8 to 1.0 microns. The surface of the spores is smooth. Whirls, synnemata, sporangia and motile spores are not observed.

2. Growth Characteristics on Various Culture Media

The standards of colors given in each of the brackets [ ] for the descriptions of colors are according to "Color Harmony Manual" of Container Corporation of America.

(1) Sucrose-nitrate agar medium (cultured at 27° C.)

Aerial hyphae of white in color are thinly formed on the growth of pale yellow [2 ea, Lt Wheat]. No soluble pigment is observed.

(2) Glycerol-asparagine agar medium (ISP-medium 5, cultured at 27° C.)

Aerial hyphae of grayish white [3 dc, Natural] to light gray [d] are formed on the growth of pale yellow [2 ea, Lt Wheat] to pale yellowish brown [2 ng, Dull Gold]. No soluble pigment is observed.

(3) Inorganic salt-starch agar medium (ISP-medium 4, cultured at 27° C.)

Aerial hyphae of white to light gray [d] are formed on the growth of pale yellow [2 ea, Lt Wheat] to pale yellowish brown [2 lg, Mustard Tan]. No soluble pigment is observed.

(4) Tyrosine agar medium (ISP-medium 7, cultured at 27° C.)

Aerial hyphae of grayish white [b, Oyster White to 3 dc, Natural] are formed on the growth of pale yellowish brown [2 le, Mustard to 2 ng, Dull Gold], with the formation of dark brown soluble pigment.

(5) Yeast extract-malt extract agar medium (ISP-medium 2, cultured at 27° C.)

Aerial hyphae of grayish white [b, Oyster White] to light gray [d] are formed on the growth of pale yellowish brown [2 ie, Lt Mustard Tan to 3 ic, Lt Amber]. No soluble pigment is observed.

(6) Oatmeal agar medium (ISP-medium 3, cultured at 27° C.)

Aerial hyphae of grayish white [3 dc, Natural] to light gray [d] are formed on the growth of pale yellow [2 ea, Lt Wheat]. No soluble pigment is observed.

3. Physiological Properties (1) Temperature range for the growing

This strain MK730-62F2 was incubated in a glucose-asparagine agar medium (containing 1.0% glucose, 0.05% asparagine, 0.05% dipotassium hydrogen phosphate and 2.5% agar, at pH 7.0) at different temperatures of 10° C., 20° C., 24° C., 27° C., 30° C., 37° C., 45° C. and 50° C. each. The results showed that this strain could grow at the temperature range of 20° C. to 37° C., excepting 10° C., 45° C. and 50° C. The optimum temperature for growth is in the vicinity of 30 to 37° C.

(2) Hydrolysis of starch (in inorganic salts-starch agar medium, ISP-medium 4, cultured at 27° C.)

The hydrolysis of starch was observed since about three days after the start of cultivation, and the degree of the hydrolytic activity is moderate.

(3) Formation of melanoid pigment (in Trypton-yeast extract broth, ISP-medium 1; peptone-yeast extract iron-agar medium, ISP-medium 6; tyrosine agar medium, ISP-medium 7; cultured at 27° C. in each medium)

Positive in all the media used.

(4) Utilization of carbon sources (in Pridham-Gottlieb agar medium, ISP-medium 9, cultured at 27° C.)

D-glucose, L-arabinose, D-fructose, sucrose, inositol, rhamnose, raffinose and D-mannitol are utilizable for the growth. D-xylose is probably utilizable.

(5) Reduction of nitrate (in aqueous peptone solution containing 0.1% potassium nitrate, ISP-medium 8, cultured at 27° C.)

Negative.

(6) Liquefaction of gelatin (in gelatin medium, cultured at 20° C.; and in glucose-peptone-gelatin medium, cultured at 27° C.)

In the gelatin medium, no liquefaction was observed during 40 days after the start of cultivation; but in the glucose-peptone-gelatin medium, weak liquefaction was observed at about 40 days after the start of cultivation.

(7) Coagulation and peptonization of skim milk (in 10% skim milk, cultured at 37° C.)

No coagulation was observed. At about 7 days after the start of cultivation, initiation of peptonization was observed and the peptonization was completed at the 14th day from the start of cultivation.

Summarizing the above-mentioned properties of the strain MK730-62F2, this strain is characterized in that it has branched substrate mycelia, from which aerial hyphae are extended with formation of spirals; that the surface of spores is smooth; that on various culture media, aerial hyphae of grayish white to light gray in color are formed on the growth of pale yellow to pale yellowish brown in color; that no soluble pigment is observed except the formation of melanoid pigment, that the optimum temperature for growth is in the vicinity of 30 to 37° C.,: that the formation of melanoid pigment is positive; and that the hydrolysis of starch is at a moderate degree. In addition, 2,6-diaminopimelic acid contained in the cell walls of this strain is of the LL-form, and the predominant menaquinone present in the bacterial cell is MK-9($H_8$) and MK-9($H_6$).

In view of these properties, it is presumed that the strain MK730-62F2 belongs to the genus Streptomyces. When searching for analogous known species with reference to the properties of this strain MK730-62F2, there have been found *Strentomyces diastatochromogenes* (Literature: International Journal of Systematic Bacteriology, Vol.22, p.290, 1972), *Streptomyces resistomycificus* (Literature: International Journal of Systematic Bacteriology, Vol.18, p.165, 1968), *Streptomyces collinus* (Literature: International Journal of Systematic Bacteriology, Vol.18, p.100 1968), and *Streptomyces aurantiogriseus* (Literature: International Journal of Systematic Bacteriology, Vol.18, p.297, 1968). Thus, we have actually examined the strain MK730-62F2 in comparison with the four strains as indicated above which were preserved in our Institute. The results are shown in Table 8 below.

TABLE 8

| | Strain MK730-62F2 | Streptomyces diastatochromogenes IMC S-0712 (ISP 5449) | Streptomyces resistomycificus IMC S-0212 (ISP 5133) |
|---|---|---|---|
| Form of aerial hyphae | Spirals | Flexous to spirals | Spirals |
| Surface of spores | Smooth | Smooth | Smooth |
| Color of aerial hyphae | Grayish white to light gray | Light gray | White to gray |
| Color of growth | Pale yellow to pale yellowish brown | Pale yellow to Pale yellowish brown | pale yellowish brown to brownish brack |
| Soluble pigment | – | – | – to brown tinged |
| Formation of melanoid pigment in | | | |
| ISP 1 medium | (+) | + | + |
| ISP 6 medium | + | + | + |
| ISP 7 medium | (+) | + | (+) |
| Reduction of nitrate | – | – | – |
| Hydrolysis of starch | + | + | + |
| Coagulation of skim milk | – | – | – |
| Peptonization of skim milk | + | (+) | – |
| Liquefaction of gelatin | – | (+) | – |
| Liquefaction of glucose-peptone-gelatin | (+) | (+) | (+) |
| Utilization of carbon sources* | | | |
| L-arabinose | + | + | + |
| D-xylose | (+) | + | (+) |
| D-glucose | + | + | + |
| D-fructose | + | + | + |
| Sucrose | + | + | + |
| Inositol | + | + | + |
| Rhamnose | + | + | + |
| Raffinose | + | + | + |
| D-mannitol | + | + | + |

| | Strain MK730-62F2 | Streptomyces collinus IMC S-0201 (ISP 5129) | Streptomyces aurantiogriseus IMC S-0069 (ISP 5138) |
|---|---|---|---|
| Form of aerial hyphae | Spirals | Straight to loops | Spirals |
| Surface of spores | Smooth | Smooth | Smooth |
| Color of aerial hyphae | Grayish white to light gray | White to grayish white | White to gray |
| Color of growth | Pale yellow to pale yellowish brown | Pale yellowish brown to light brown | Pale yellowish brown to light brown |
| Soluble pigment | – | – | – to brown tinged |
| Formation of melanoicl pigment in | | | |
| ISP 1 medium | (+) | (+) | + |
| ISP 6 medium | + | + | + |
| ISP 7 medium | (+) | (+) | (+) |
| Reduction of nitrate | – | – | + |
| Hydrolysis of starch | + | + | + |
| Coagulation of skim milk | – | – | – |
| Peptonization of skim milk | + | – | + |
| Liquefaction of gelatin | – | – | (+) |
| Liquefaction of glucose-peptone-gelatin | (+) | (+) | (+) |
| Utilization of carbon sources* | | | |
| L-arabinose | + | + | + |
| D-xylose | (+) | (+) | (+) |
| D-glucose | + | + | + |
| D-fructose | + | + | + |
| Sucrose | + | + | (+) |
| Inositol | + | + | (+) |
| Rhamnose | + | (+) | + |
| Raffinose | + | + | + |
| D-mannitol | + | + | + |

(Notes)
*+: Utilizable;
(+): Probably utilizable;
(±): Doubtful, either utilizable or not utilizable.

As is clear from Table 8 above, the strain MK730-62F2 has properties which closely resemble to those of any of the strains which are compared therewith in Table 8. However, *Streptomyces resistomycificus* is different from the strain MK730-62F2 in that, with *Streptomyces resistomycificus*, the color of the growth is pale yellowish brown to brownish black, the soluble pigment is tinged with brown, and skim milk is not peptonized. *Streptomyces collinus* is different from the strain MK730-62F2 in that, with the former species, the form of aerial hyphae is straight to loop, and skim milk is not peptonized. *Streptomyces aurantiogriseus* is distinguished from the strain MK730-62F2 in that, with the former species, the soluble pigment is tinged with brown, gelatin is liquefied and nitrate is reduced. On the other hand, *Streptomyces diastatochromogenes* resembles very closely to the strain MK730-62F2, except that the liquefaction of gelatin is positive with the former species. At this time, however, it is impossible that the strain MK730-62F2 is identified as one strain which belongs to *Streptomyces diastatochromogenes*. So, we have designated the strain MK730-62F2 as Streptomyces sp. MK730-62F2.

The strain MK730-62F2 has been deposited in a Japanese depository "National Institute of Bioscience and Human-Technology, Agency of Industrial Science and Technology" located at No.1–3, Higashi 1-chome, Tsukuba-City, Ibaraki-ken, Japan, under the deposit number "FERM P-17067 on Nov. 27, 1998. This strain has now been deposited under the deposit number "FERM BP-7218" in said National Institute as transferred in terms of the Budapest Treaty.

According to the second aspect process of this invention, the production of the antibiotic, caprazamycins may be carried out as described below.

Thus, the production of the antibiotic, caprazamycins is carried out by inoculating a microbial strain capable of producing at least one of the antibiotic caprazamycins A, B, C, E and E (this strain is referred hereinafter to simply as "a caprazamycin-producing strain") in a nutrient medium, and cultivating said microbial strain at an appropriate temperature to produce the antibiotic, a caprazamycin, whereby the culture containing the antibiotic caprazamycins is obtained.

As the nutrient medium to be used for this purpose, there may be used any nutrient medium which is usable for the cultivation of actinomycetes. As the nutrient sources, there may be used nitrogen sources, for example, soybean flour, peptone, yeast extract, meat extract, corn steep liquor, ammonium sulfate and others which are commercially available. As carbon sources, there may be used carbohydrates such as tomato paste, glycerin, starch, glucose, galactose, dextrin and others, as well as fats and the like. Further, there may be used inorganic salts such as sodium chloride, calcium carbonate and the like, as additives. If necessary, other additives, for example, metal salts may be added in a very small amount. These additive substances may be any of those materials which are utilizable by a caprazamycin-producing strain and are useful for the production of the antibiotic caprazamycins, and which are known to be utilizable in the culture media for the cultivation of actinomycetes.

For the production of the antibiotic caprazamycins, there may be used a microorganism which belongs to the genus Streptomyces and has an ability to produce the antibiotic caprazamycins. Specifically, the Streptomyces sp. MK730-62F2 as isolated by us has been confirmed to produce the antibiotic caprazamycins. Any other strain capable of producing said antibiotics is possible to be isolated from the nature by employing any known isolation technique which are available for the isolation of the antibiotic-producing strains. There still remains such possibility that the ability of a caprazamycin-producing strain, including Streptomyces sp. MK730-62F2, to produce the antibiotic caprazamycins is improved by subjecting such strain to a mutation treatment with radio-active radiation or others. Further, the antibiotic caprazamycins may be produced by a genetic engineering technique.

As a seed culture to be used for the production of caprazamycins, there may be used a growth which is obtained from a slant culture of the strain MK730-62F2 on an agar medium.

Upon the production of the antibiotic caprazamycins, it is preferable that a caprazamycin-producing strain belonging to the genus Streptomyces is cultivated in a suitable culture medium under aerobic conditions. The recovery of the desired caprazamycins(s) from the resulting culture broth may be effected in a conventional manner. The cultivation temperature is not specifically limited, so far as it is within the range of temperatures at which the desired antibiotics can be produced without substantially preventing the growth of the caprazamycin-producing strain as used. The cultivation temperature may be chosen depending upon the nature of a caprazamycin-producing strain as used, and a preferred cultivation temperature is in a range of 25 to 30° C.

The production of caprazamycins by the strain MK730-62F2 can usually reach a maximum for 3 to 9 days of the cultivation of the strain. In general, however, the cultivation of the strain is continued until a sufficient antibacterial activity is given to the culture medium. The time-dependent change in the potency of caprazamycins in the resulting culture broth may be measured either by HPLC method, or by a cylinder plate method in which *Mycobacterium smegmatis* or *Mycobacterium vaccae* is used as an assaying strain.

In the second aspect process of this invention, at least one of caprazamycins A, B, C, E and F is recovered from the culture broth which has been obtained as above. As the method for recovering and isolating the desired caprazamycin(s), there may appropriately be used any of conventional methods which are used for the isolation of metabolite(s) as produced by microorganisms. For example, a method for extraction with an organic solvent immiscible with water, and a method for utilizing the difference in the adsorption affinities of the caprazamicins onto various adsorbents, such as a synthetic adsorbent resin, silica gel and a method for gel filtration and chromatographic method with countercurrent distribution, etc. may be used, singly or in combination, in order to recover caprazamycin(s) A, B, C, E and/or F, either singly or in the form of a mixture of any two or more of them, from the culture broth supernatant. Further, from the microbial cells of the strain so separated from the culture broth, it is also possible to recover caprazamycin(s) A, B, C, E and/or F, by subjecting the microbial cells to a solvent extraction with a suitable organic solvent, or by a method comprising disrupting the cells and eluting the desired caprazamycin(s) out of the disrupted cells by extraction. Incidentally, the antibiotic caprazamycin(s) A, B, C, E and/or F may be harvested, separately or in combination. Incidentally, the isolation of caprazamycins A, B, C, E and F from each other may be effected by a high performance liquid chromatography (HPLC) with a suitable development solvent.

Further, according to a third aspect of this invention, there is provided a pharmaceutical composition which comprises as an active ingredient at least one of caprazamycins A, B, C, E and F having the general formula (I) or a salt thereof, in admixture with a pharmaceutically acceptable carrier or carriers.

The pharmaceutical composition according to the third aspect of this invention may be in the form of a composition which comprises as the active ingredient a compound of the general formula (I), in admixture with a conventional, pharmaceutically acceptable solid or liquid carrier, for example, ethanol, water, physiological saline, starch and the like.

Caprazamycin(s) of the general formula (I) or a salt thereof, which is or are to be used in the pharmaceutical composition according to the third aspect of this invention, may be administered orally or parenterally by intravenous, intramuscular or intraperitoneal administration, and so on.

For the oral administrations, the pharmaceutical composition according to the third aspect of this invention may be formulated in the form of preparations such as powder, tablets, capsules, suspension, syrup and the like, by blending the active ingredient, namely a caprazamycin of general formula (I) or a salt thereof, with a conventional, pharmaceutically acceptable solid or liquid carrier.

The proportion of the compound of the general formula (I) which is incorporated as the active ingredient in the pharmaceutical composition of the third aspect of this invention may depend upon the type of the preparations, but a convenient proportion of a caprazamycin may be in the range of about 2 to 90%, based on the weight of the dosage unit of the composition.

In cases where the composition of the third aspect of this invention is formulated into injections, a preferred form of the injectionable preparations may include a sterilized aqueous solution or a sterilized and lyophilized preparation which contains the compound of the general formula (I) as active ingredient. As examples of the liquid carriers usable for this purpose, water, aqueous ethanol, glycerol, propylene glycol, vegetable oil and the like are preferred.

The dose of a caprazamycin of the general formula (I) or a salt thereof as an active ingredient in the composition of this invention may depend upon the nature of bacterial infections to be treated, a purpose of the therapeutic treatment, degree of the patient's conditions and so on. However, an optimal dose of a caprazamycin can be decided by experts through suitable preliminary tests. By the way, caprazamycin B did not exhibit any toxicity in mice (ICR type, 4 weeks-aged, male), when administered intravenously at a dose of 75 mg/kg.

According to a fourth aspect of this invention, there is further provided, as a novel microorganism, Streptomyces sp. MK730-62F2 which has a characteristic nature that it is capable of producing caprazamycins A, B, C, E and F of general formula (I) above, and which has been deposited in the "National Institute of Bioscience and Human-Technology, Agency of Industrial Science and Technology" as located at No. 1–3, Higashi 1-chome, Tsukuba-City, Ibaraki-Prefecture, Japan, under the deposit number "FERM BP-7218".

BRIEF DESCRIPTION OF ATTACHED DRAWINGS

BEST MODE FOR CARRYING OUT THE INVENTION

Figure 1:
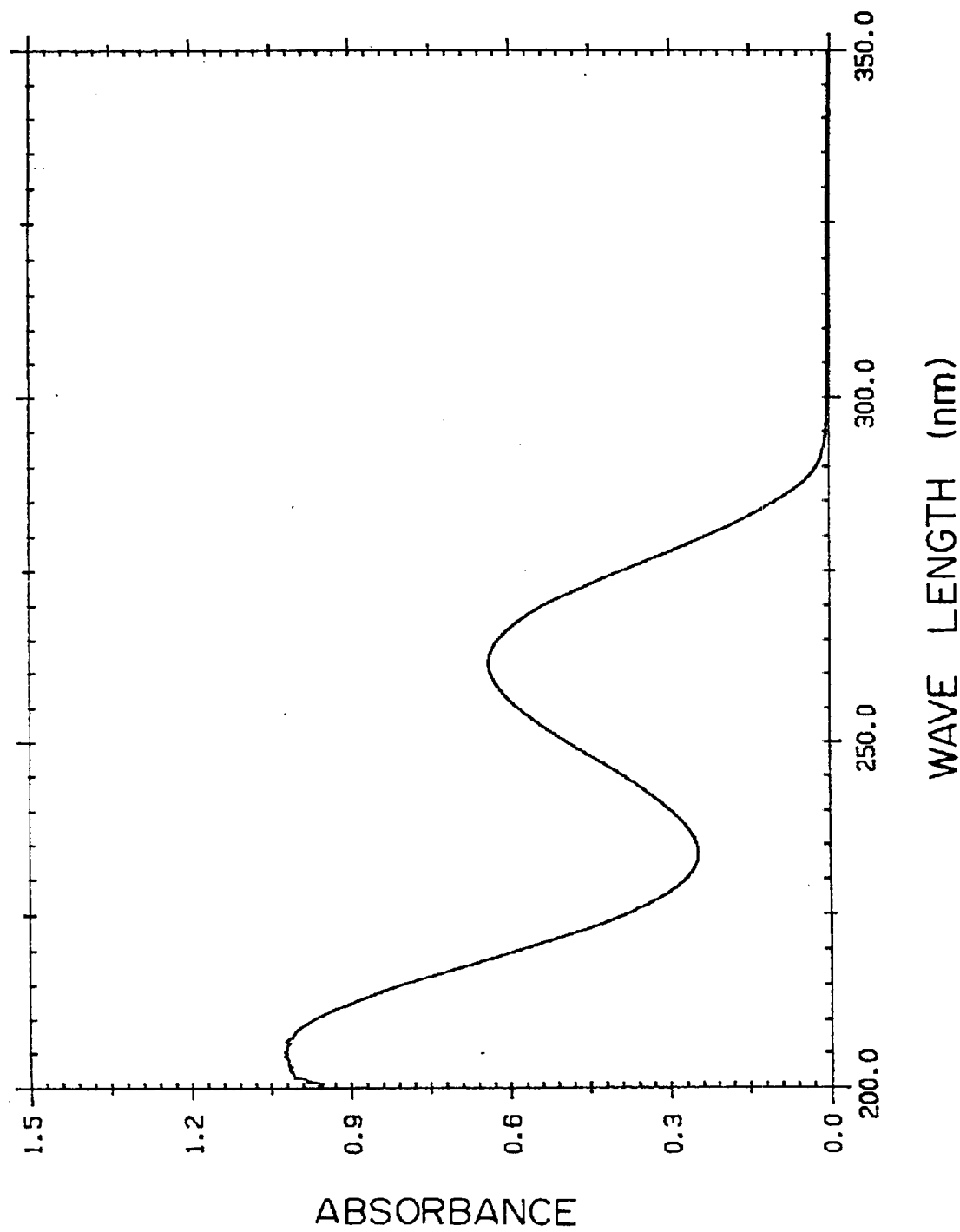
FIG. 1 is ultraviolet absorption spectrum of caprazamycin A in a methanolic solution.
Figure 2:
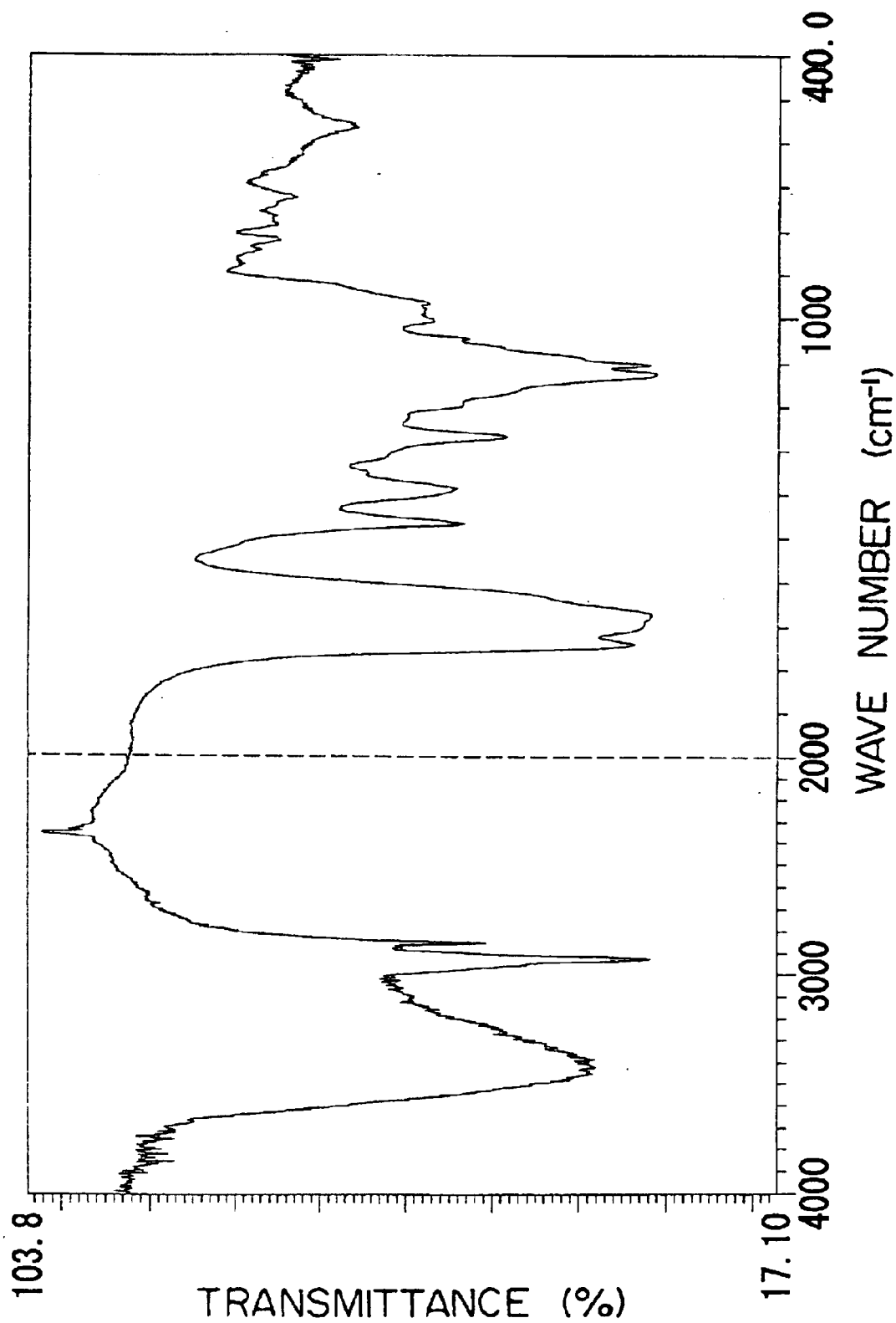
FIG. 2 is infrared absorption spectrum of caprazamycin A as measured by KBr-tableted method.
Figure 3:
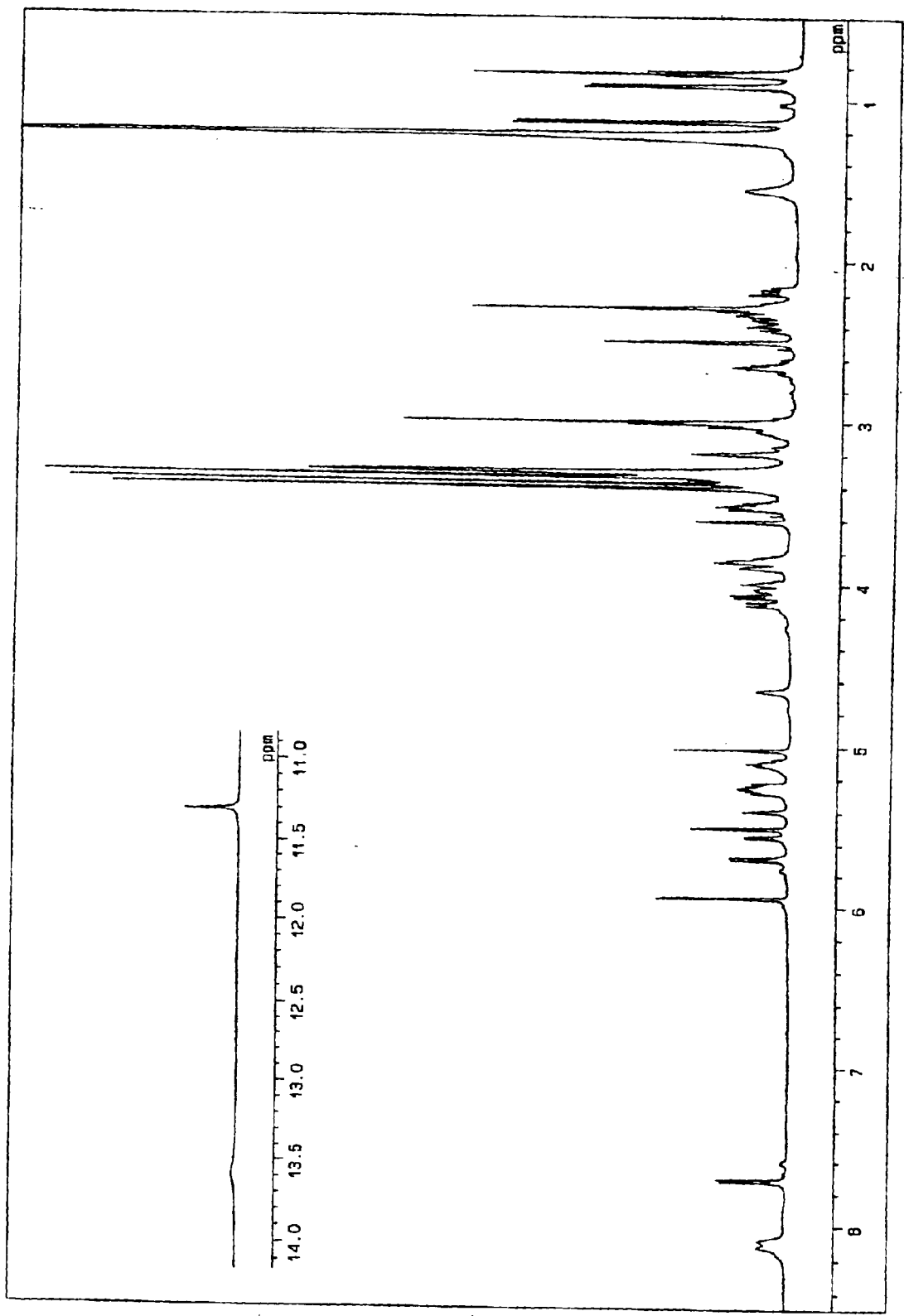
FIG. 3 is proton nuclear magnetic resonance spectrum of caprazamycin A as measured in DMSO-$d_6$ solution at 500 MHz at room temperature.
Figure 4:
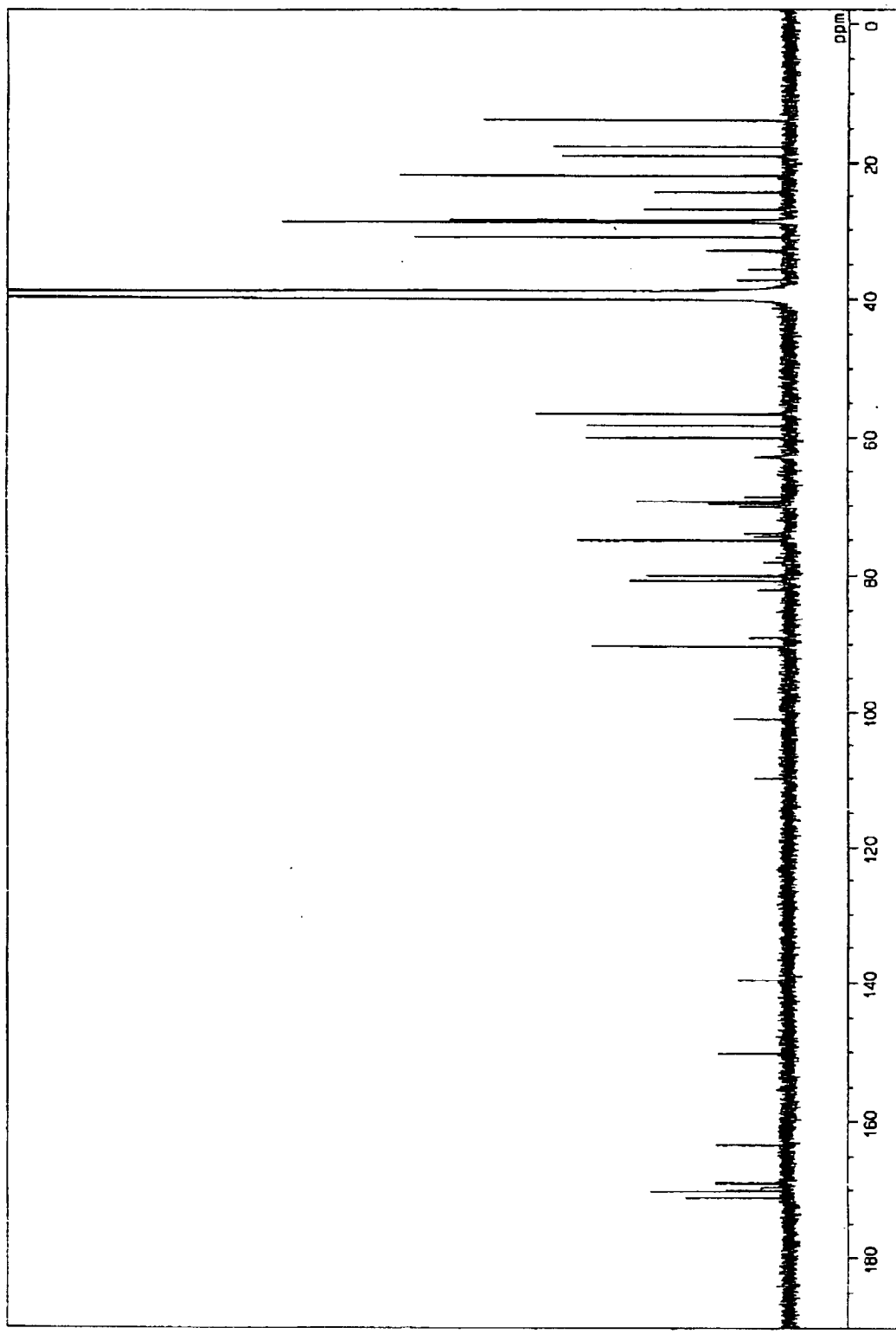
FIG. 4 is $^{13}$C-nuclear magnetic resonance spectrum of caprazamycin A as measured in DMSO-$d_6$ solution at 125 MHz at room temperature.
Figure 5:
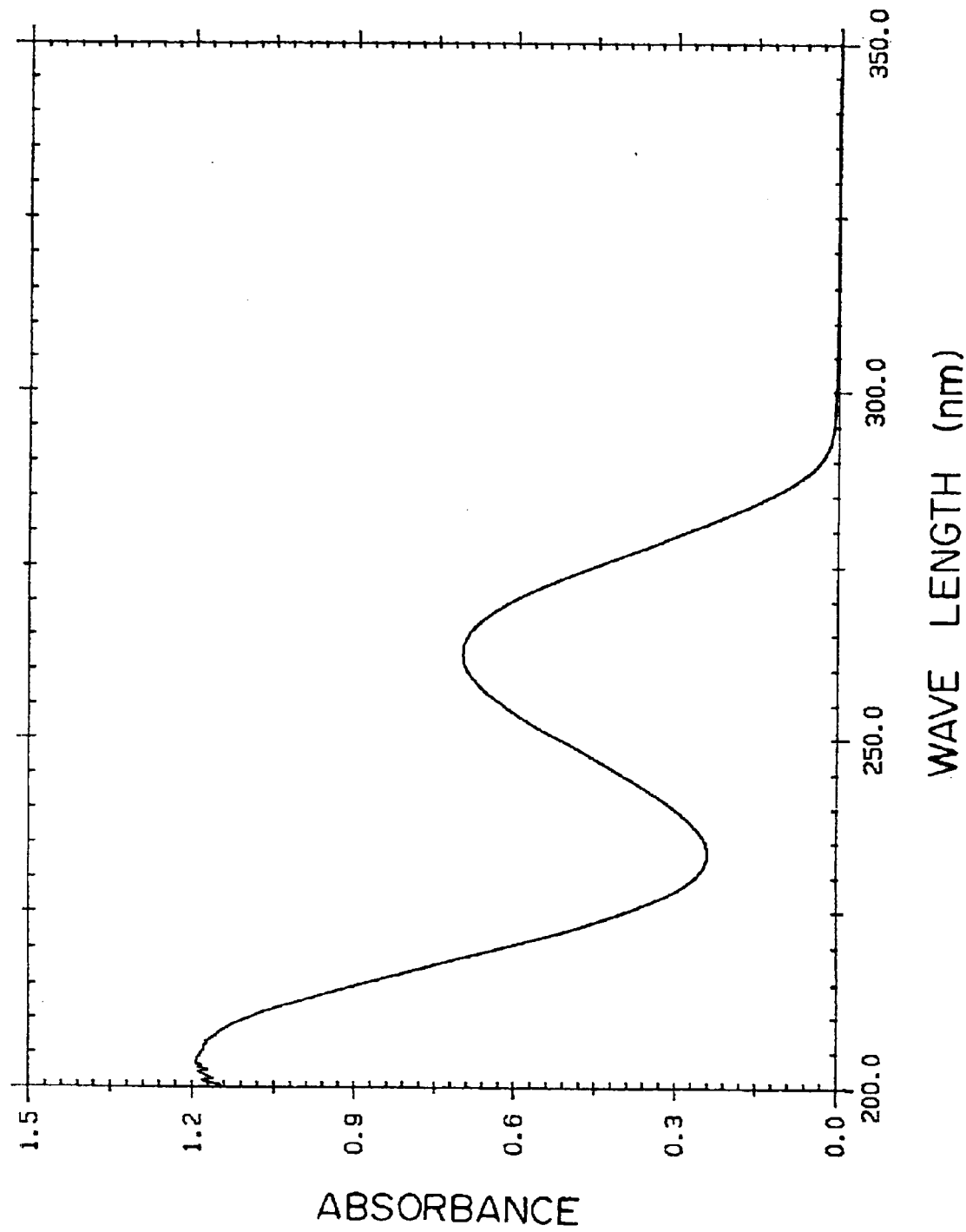
FIG. 5 is ultraviolet absorption spectrum of caprazamycin B in a methanolic solution.
Figure 6:
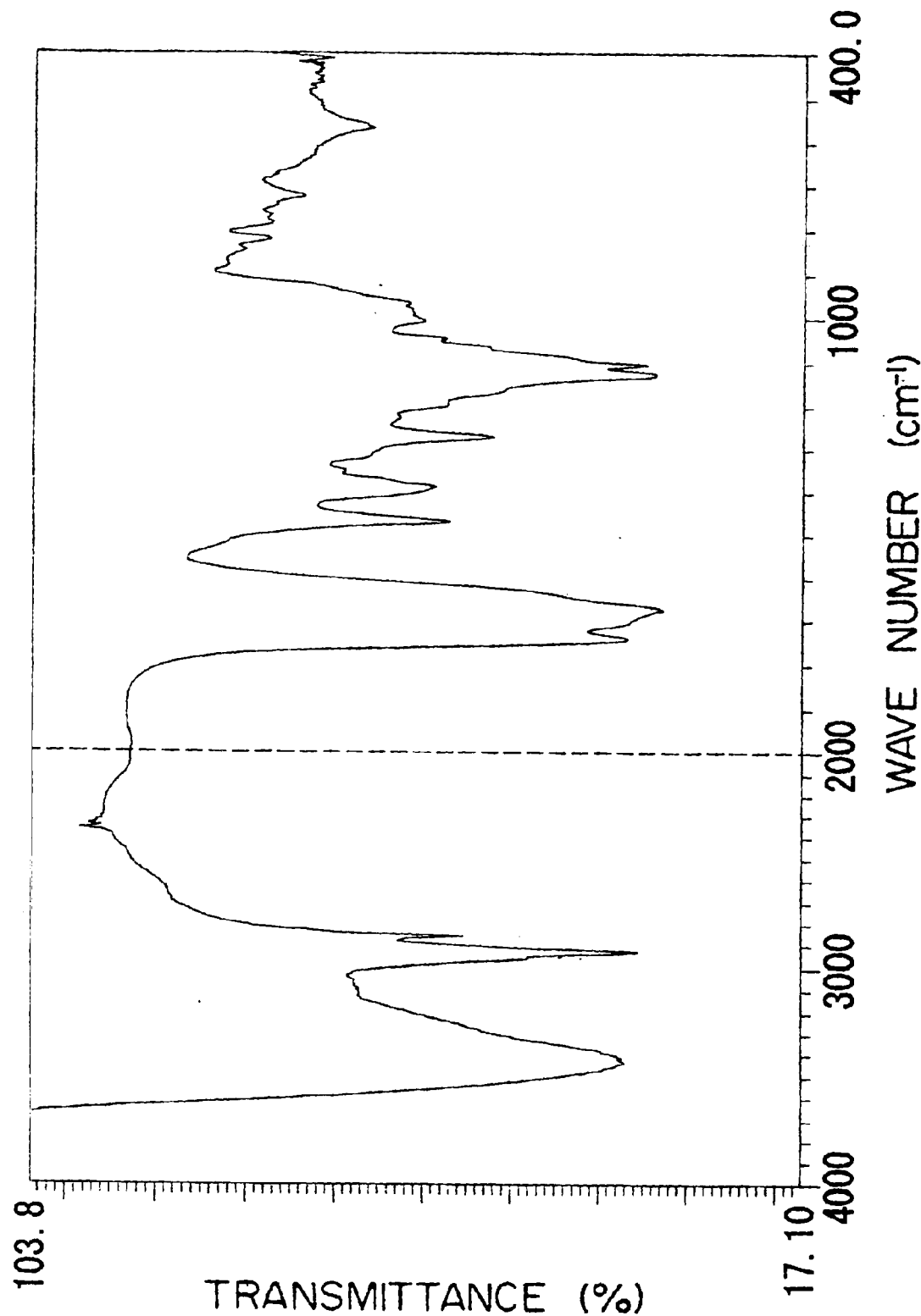
FIG. 6 is infrared absorption spectrum of caprazamycin B as measured by KBr-tableted method.
Figure 7:
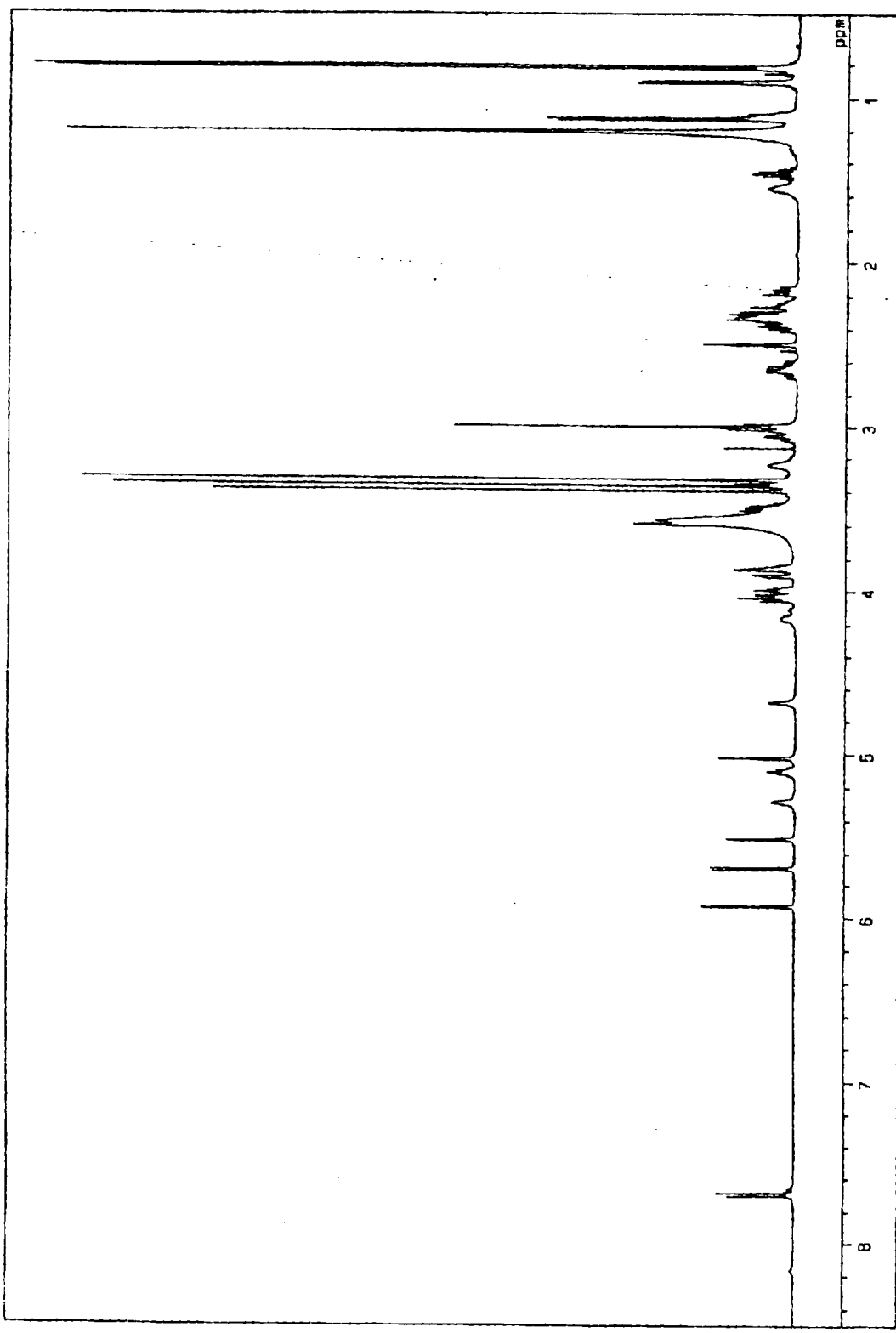
FIG. 7 is proton nuclear magnetic resonance spectrum of caprazamycin B as measured in a mixed solvent of DMSO-$d_6$-$D_2O$ (10:1) at 500 MHz at room temperature.
Figure 8:
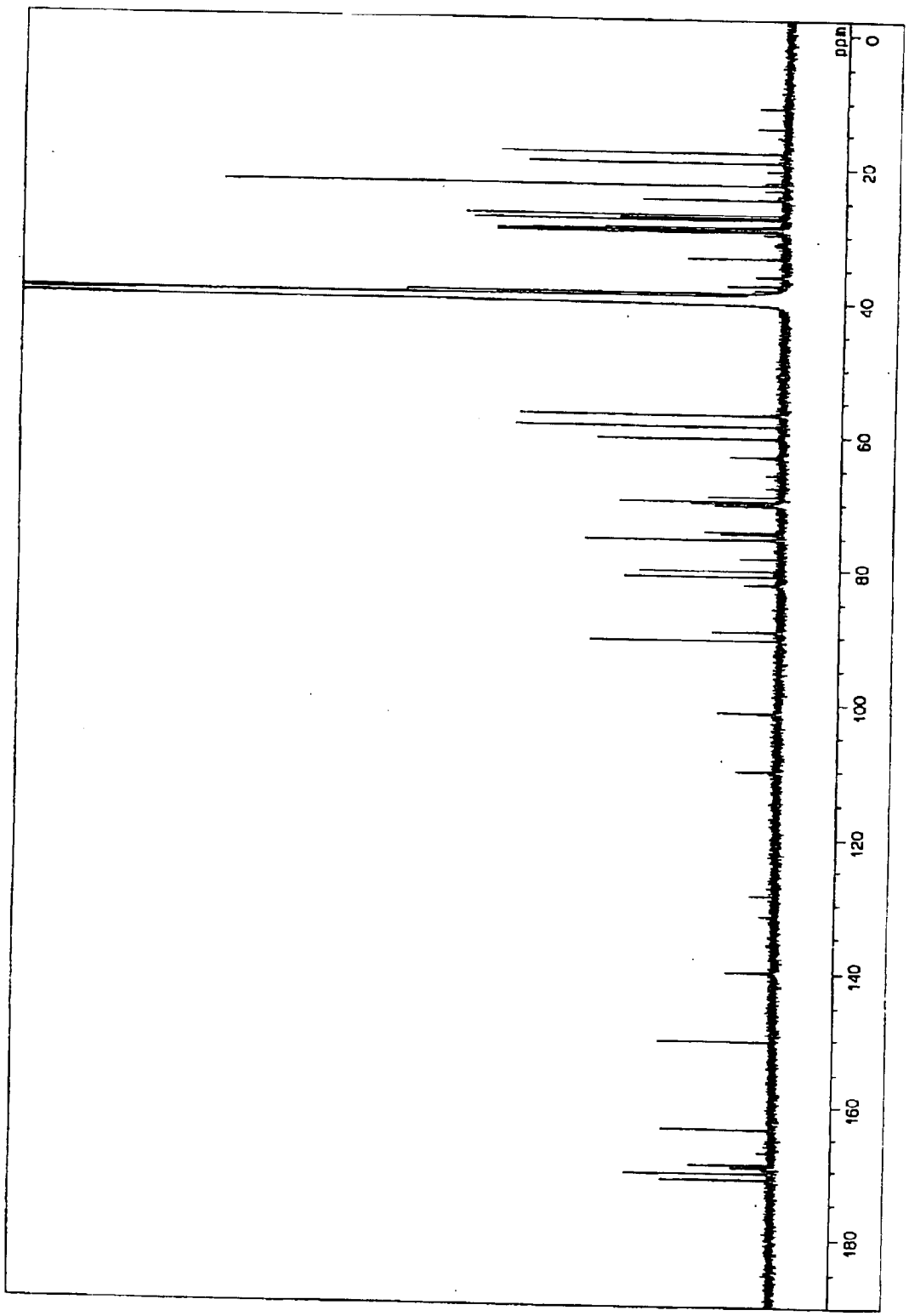
FIG. 8 is $^{13}$C-nuclear magnetic resonance spectrum of caprazamycin B as measured in a mixed solvent of DMSO-$d_6$-$D_2O$ (10:1) at 125 MHz at room temperature.
Figure 9:
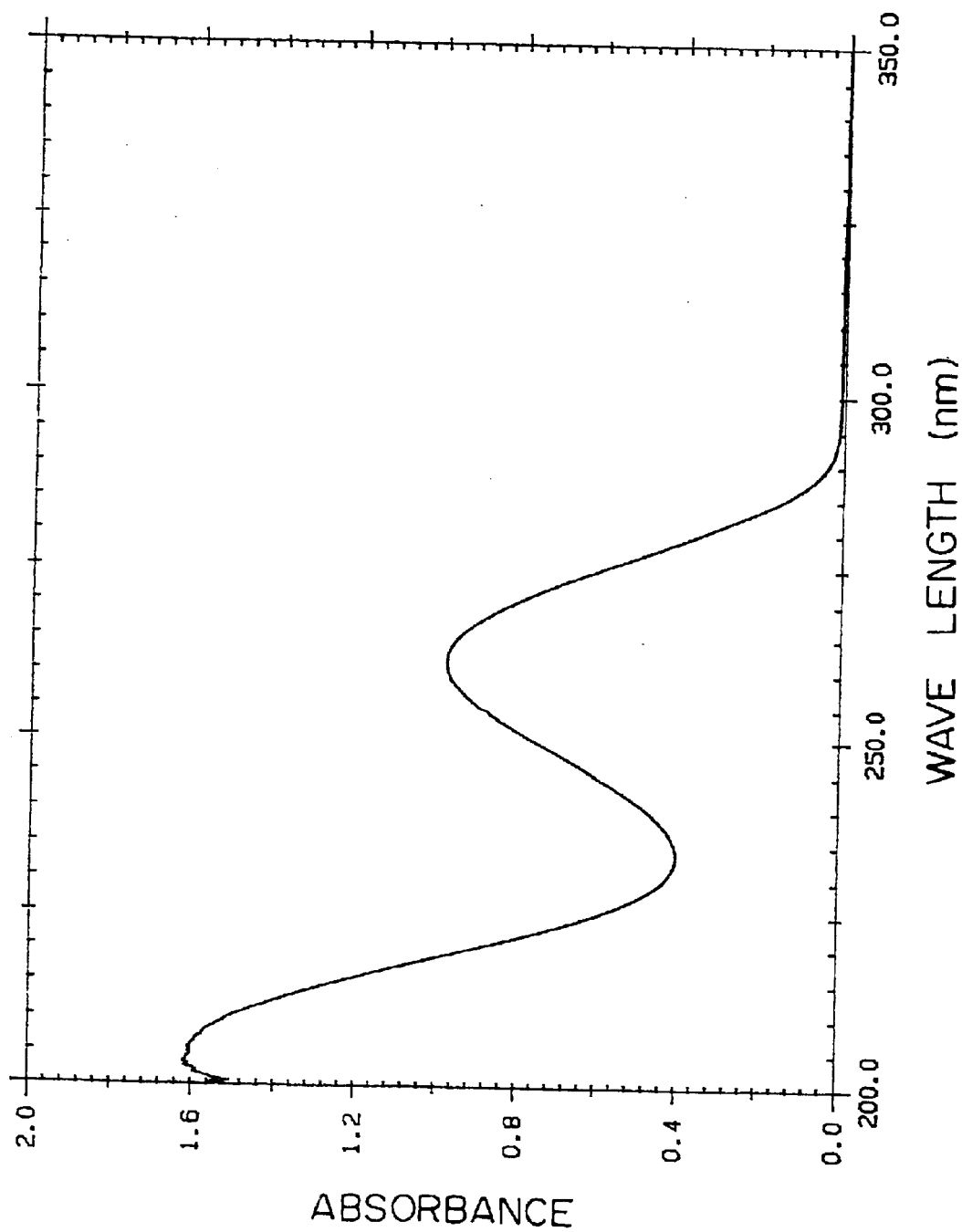
FIG. 9 is ultraviolet absorption spectrum of caprazamycin C in a methanolic solution.
Figure 10:
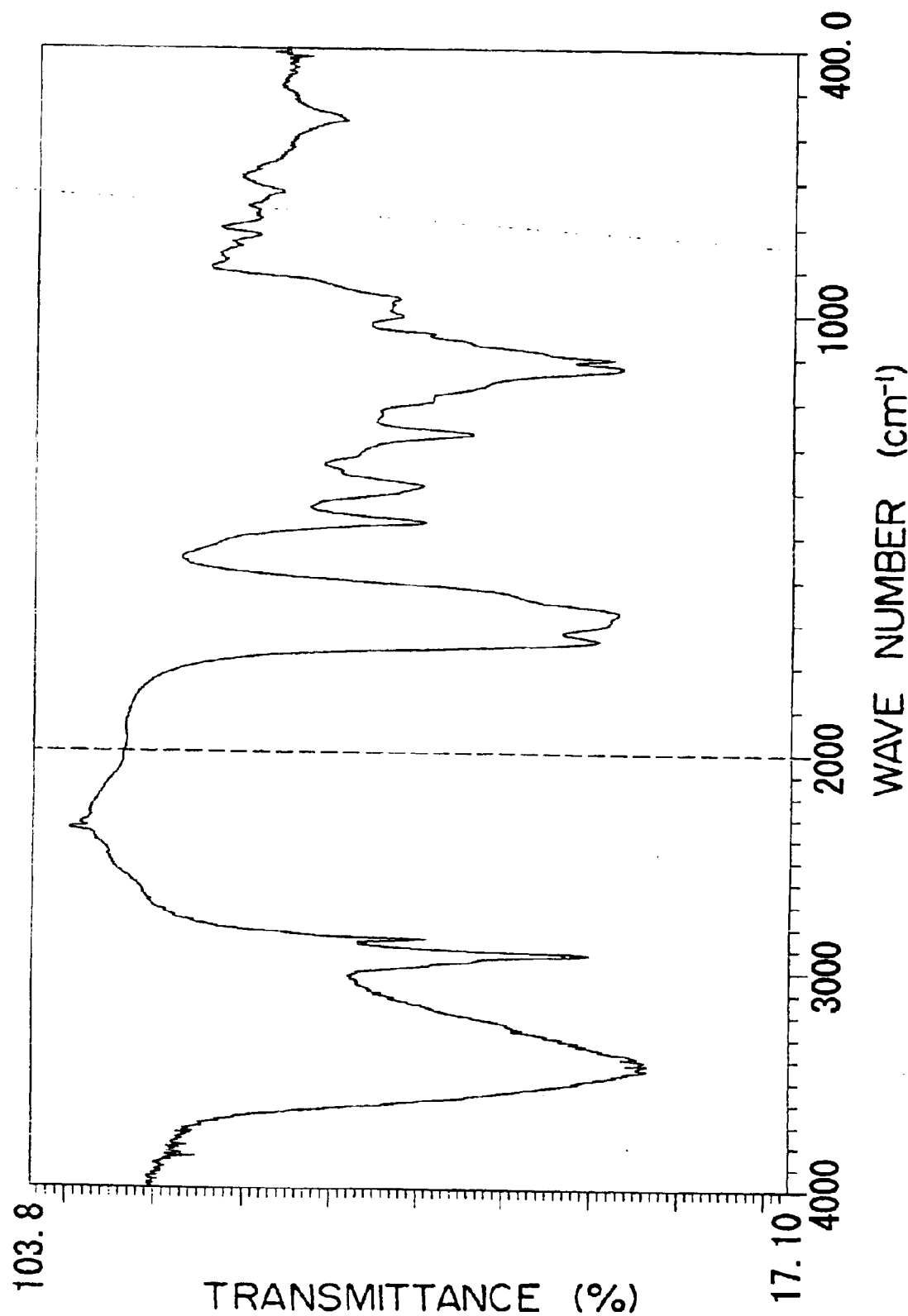
FIG. 10 is infrared absorption spectrum of caprazamycin C as measured by KBr-tableted method.
Figure 11:
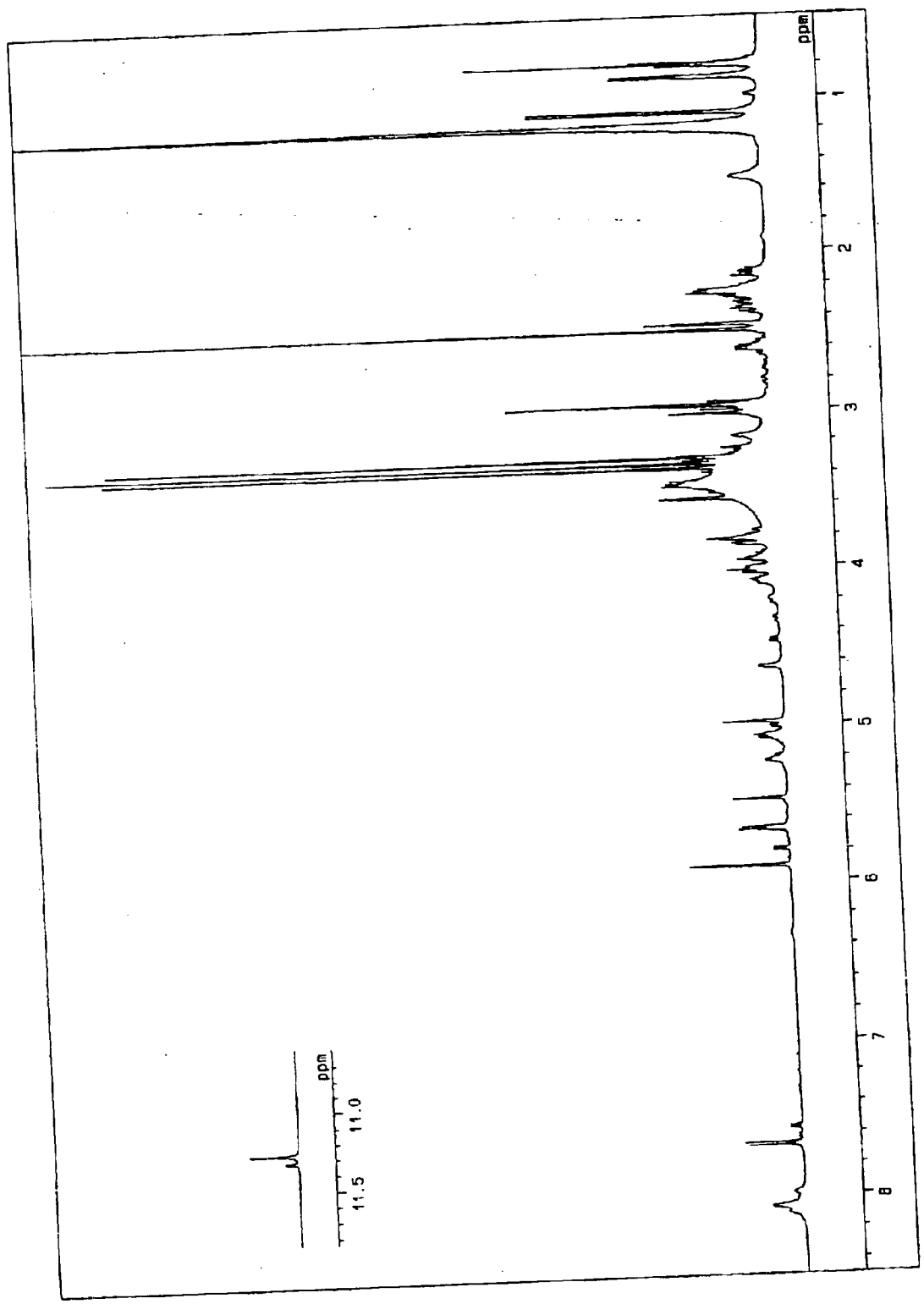
FIG. 11 is proton nuclear magnetic resonance spectrum of caprazamycin C as measured in DMSO-$d_6$ solution at 500 MHz at room temperature.
Figure 12:
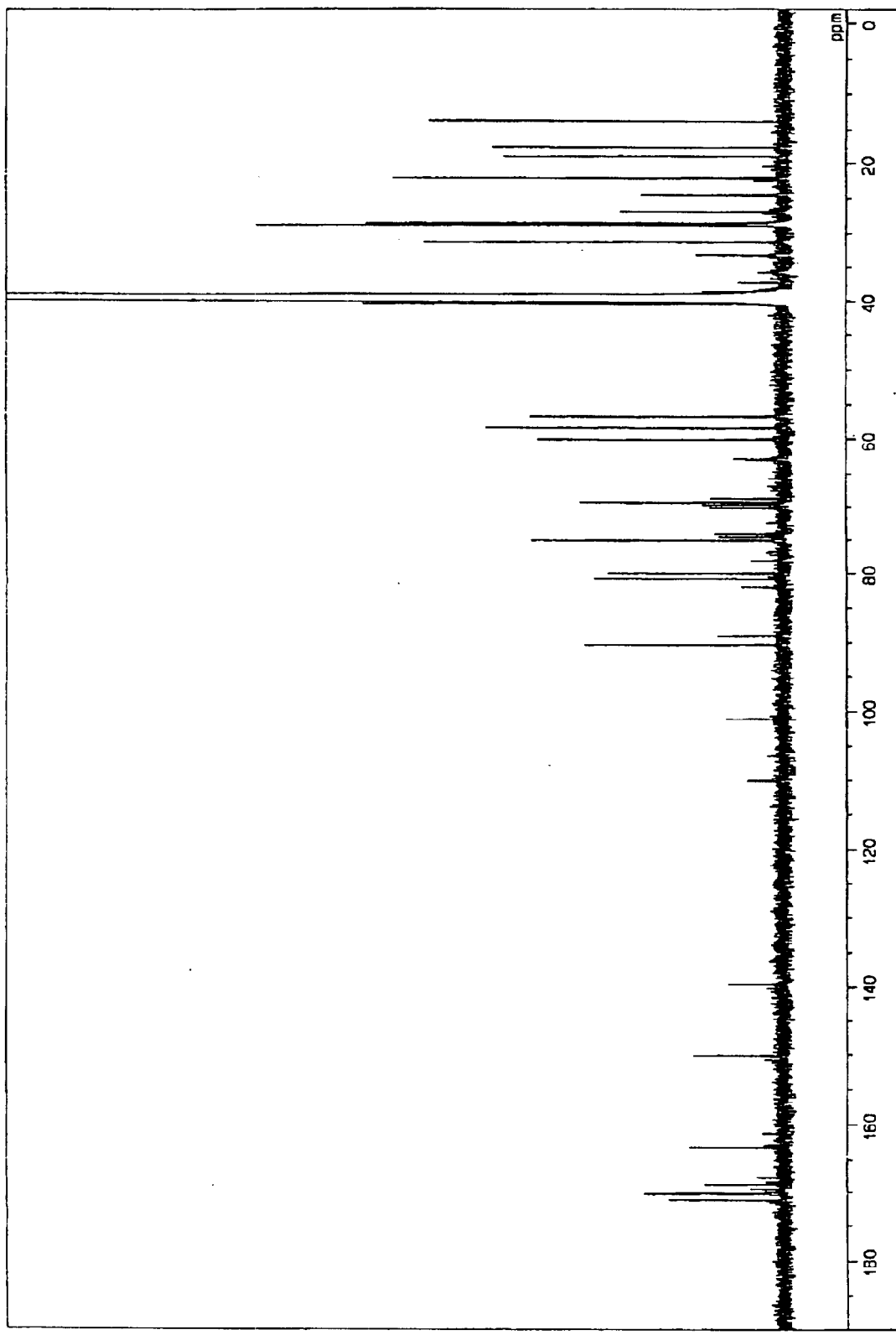
FIG. 12 is $^{13}$C-nuclear magnetic resonance spectrum of caprazamycin C as measured in DMSO-$d_6$ solution at 125 MHz at room temperature.
Figure 13:
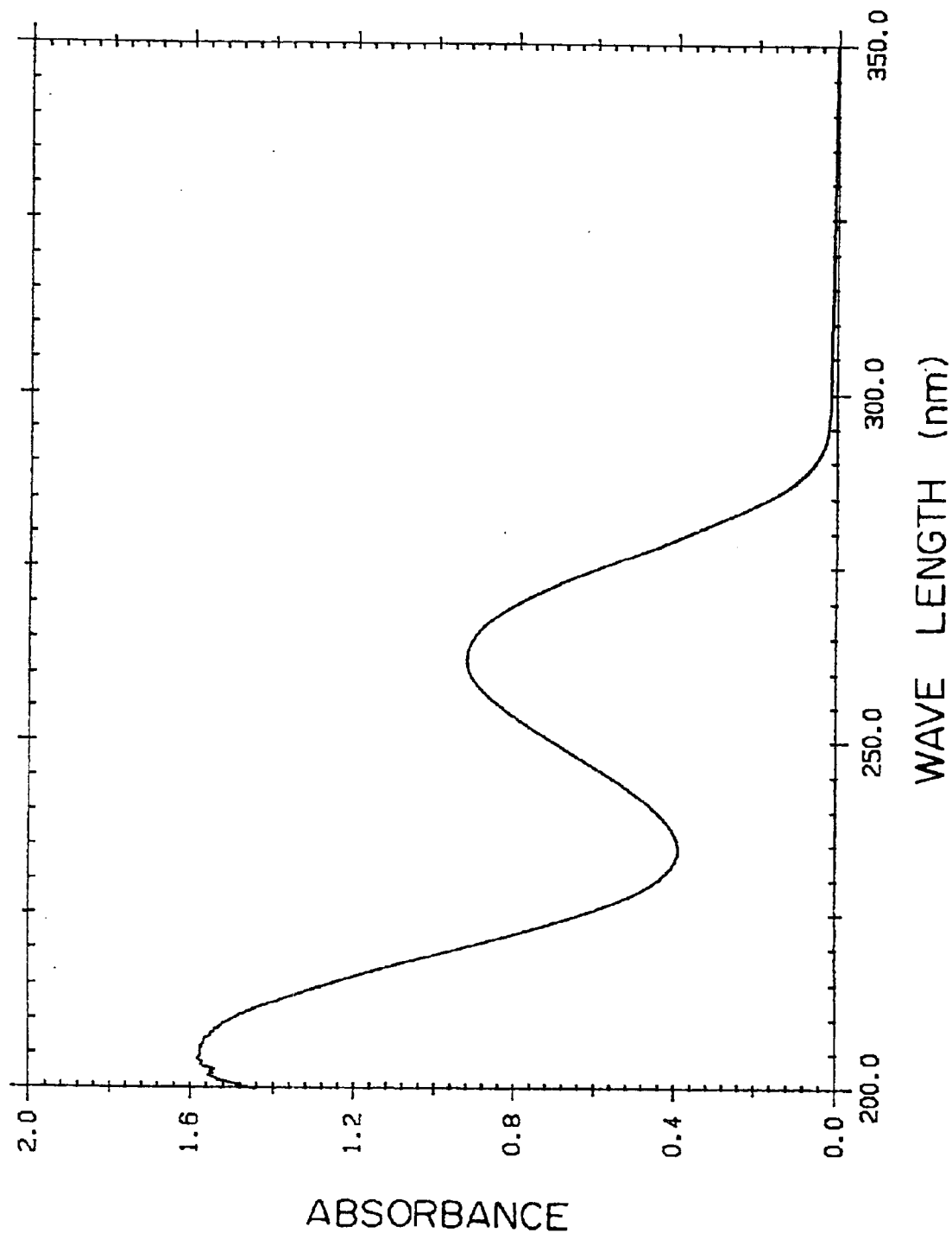
FIG. 13 is ultraviolet absorption spectrum of caprazamycin E in a methanolic solution.
Figure 14:
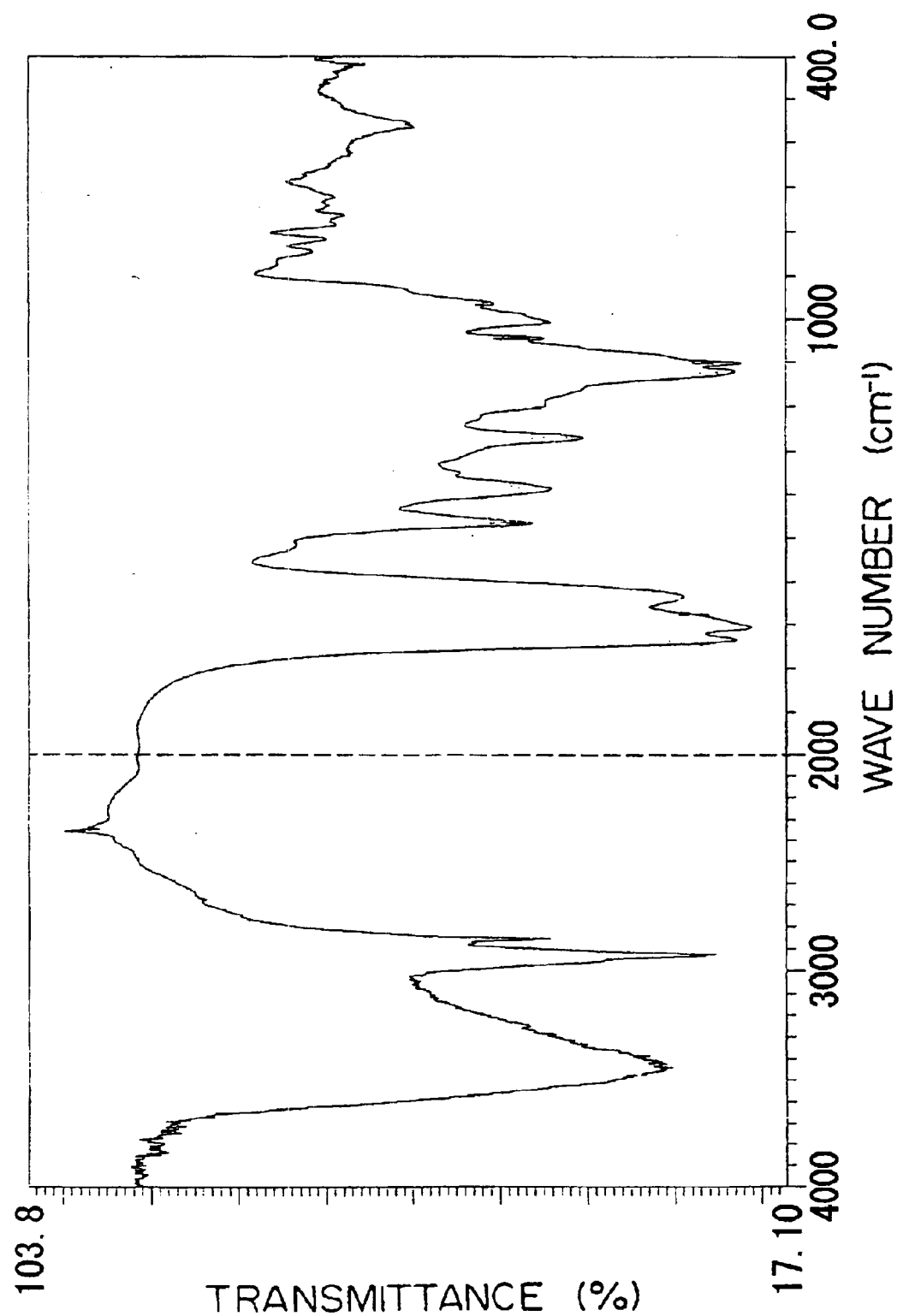
FIG. 14 is infrared absorption spectrum of caprazamycin E as measured by KBr-tableted method.
Figure 15:
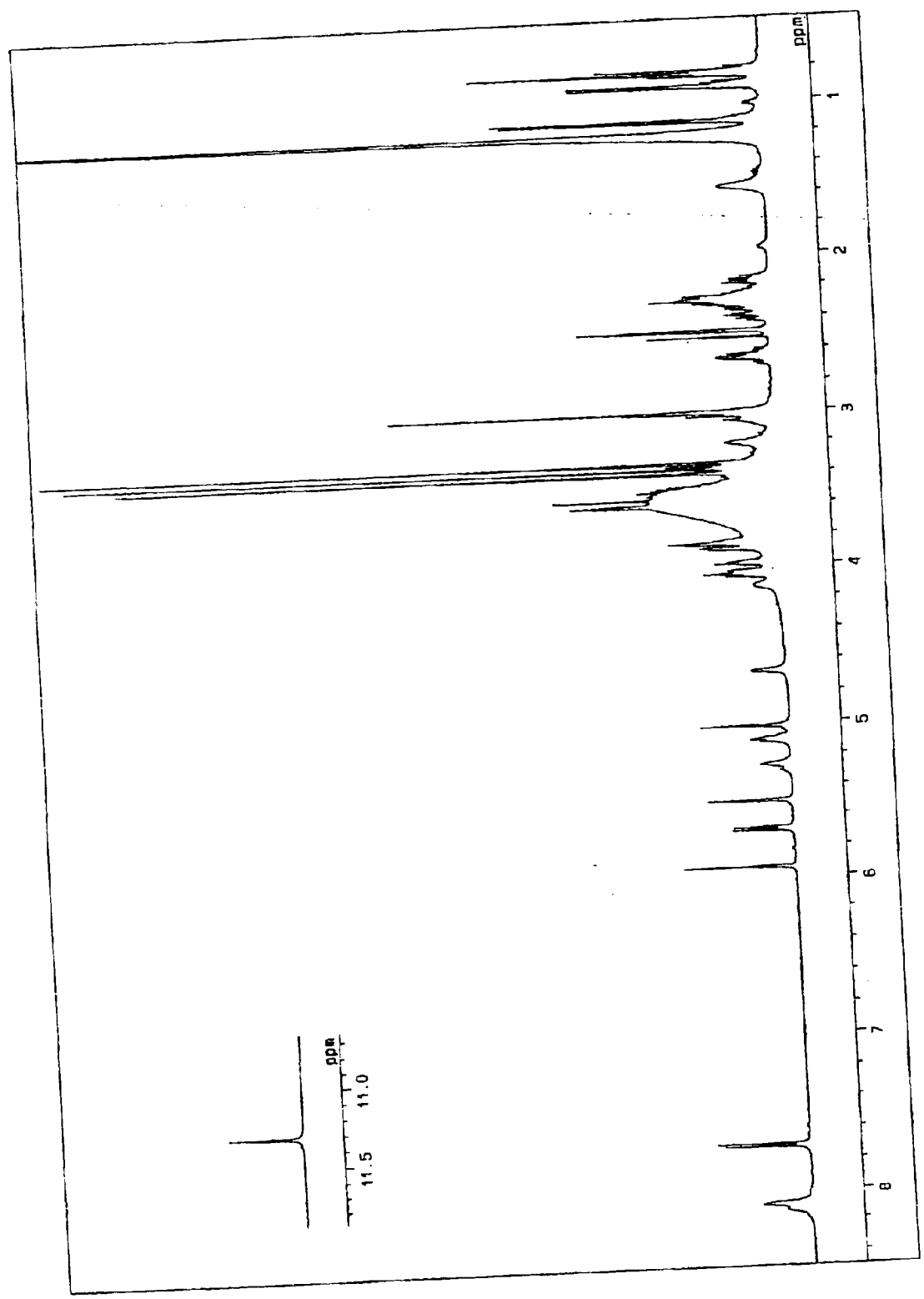
FIG. 15 is proton nuclear magnetic resonance spectrum of caprazamycin E as measured in DMSO-$d_6$ solution at 500 MHz at room temperature.
Figure 16:
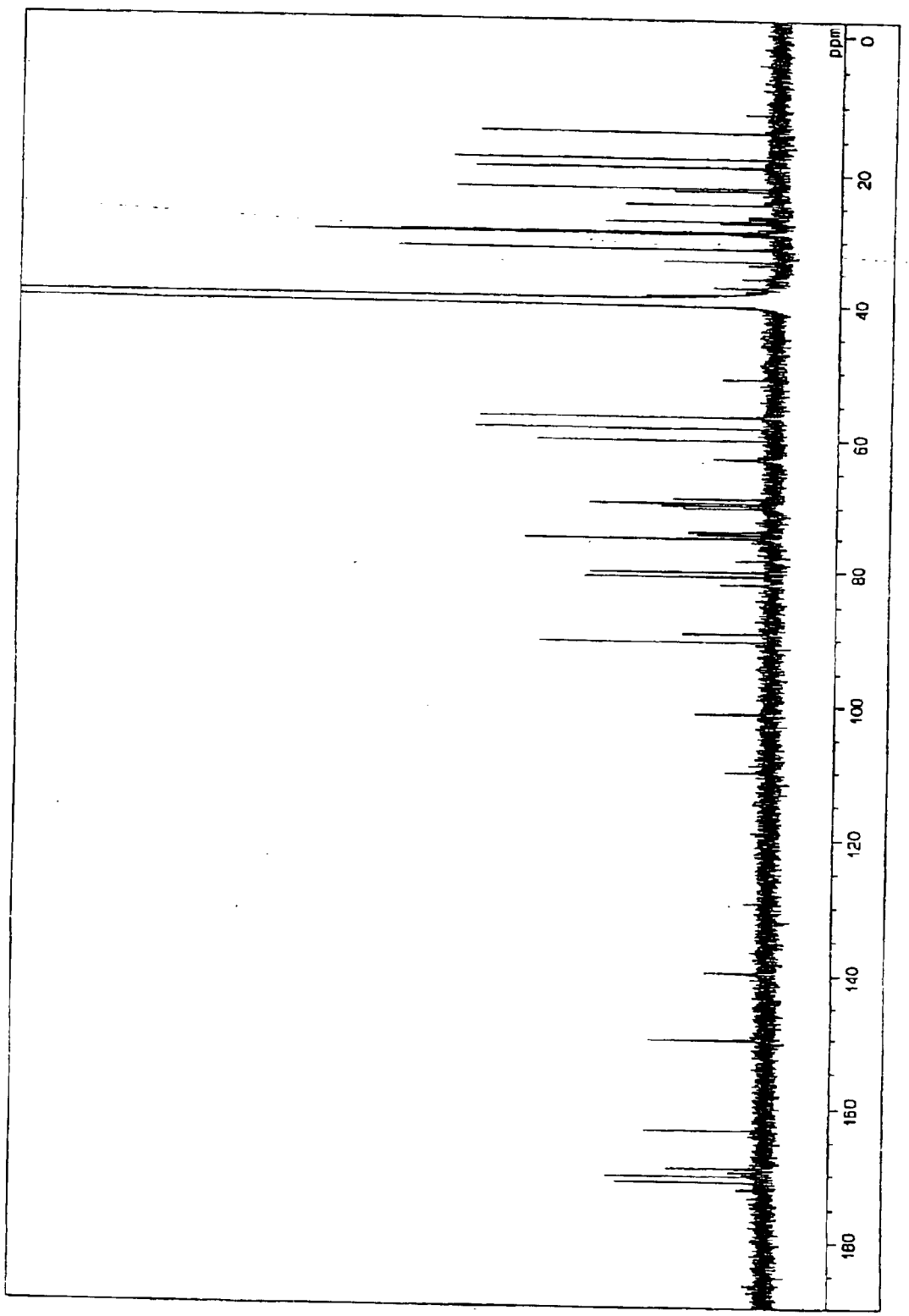
FIG. 16 is $^{13}$C-nuclear magnetic resonance spectrum of caprazamycin E as measured in DMSO-$d_6$ solution at 125 MHz at room temperature.
Figure 17:
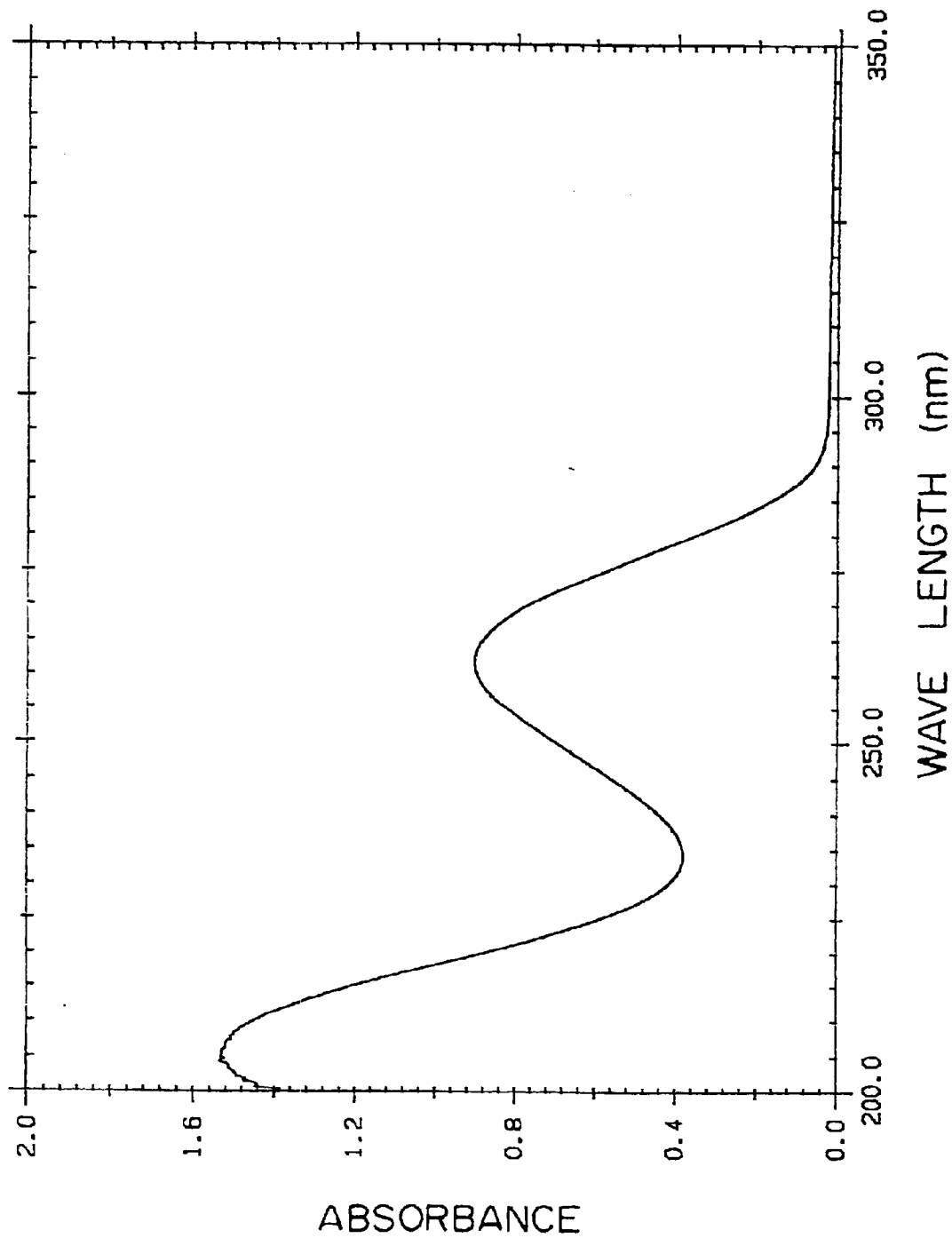
FIG. 17 is ultraviolet absorption spectrum of caprazamycin F in a methanolic solution.
Figure 18:
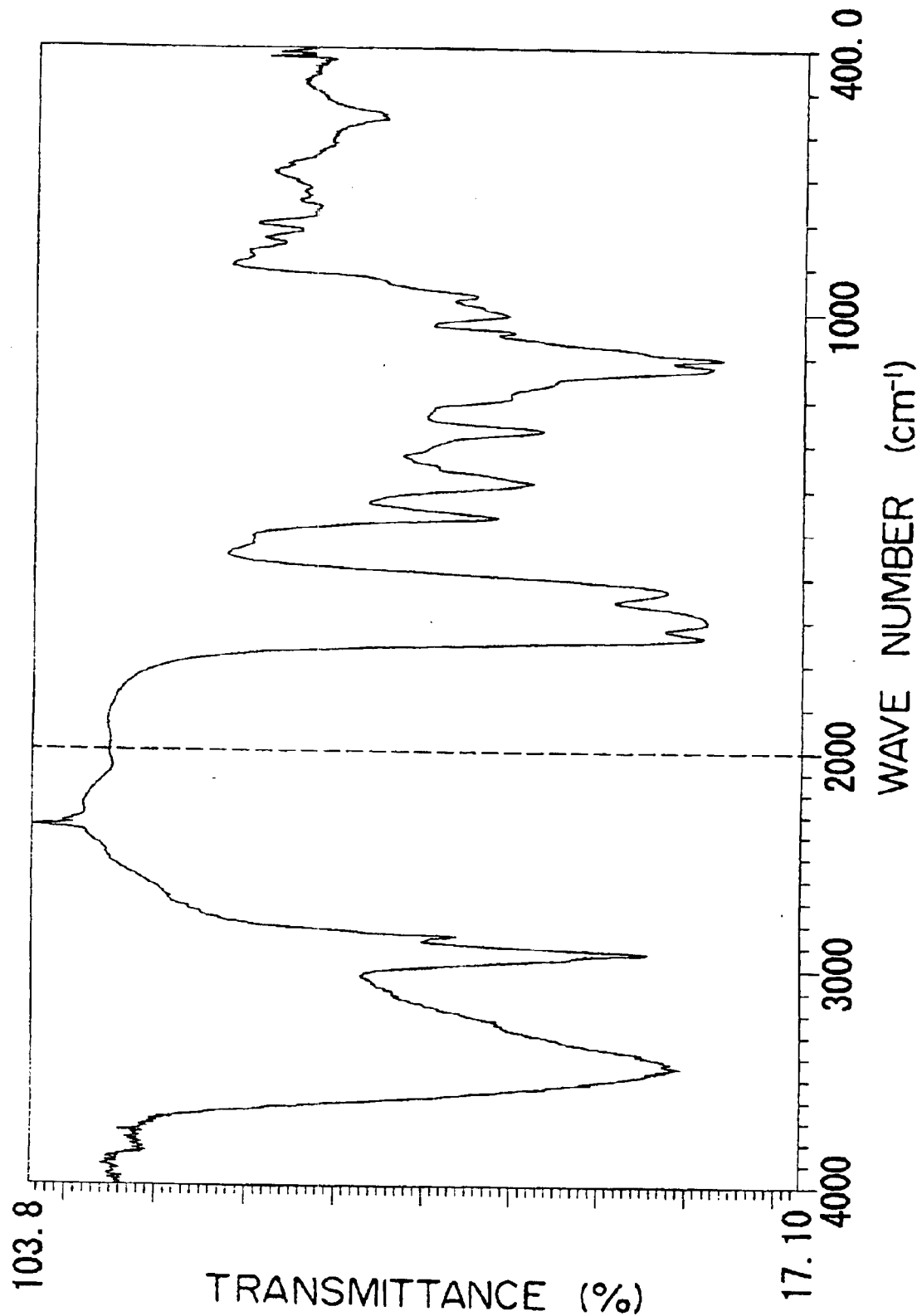
FIG. 18 is infrared absorption spectrum of caprazamycin F as measured by KBr-tableted method.
Figure 19:
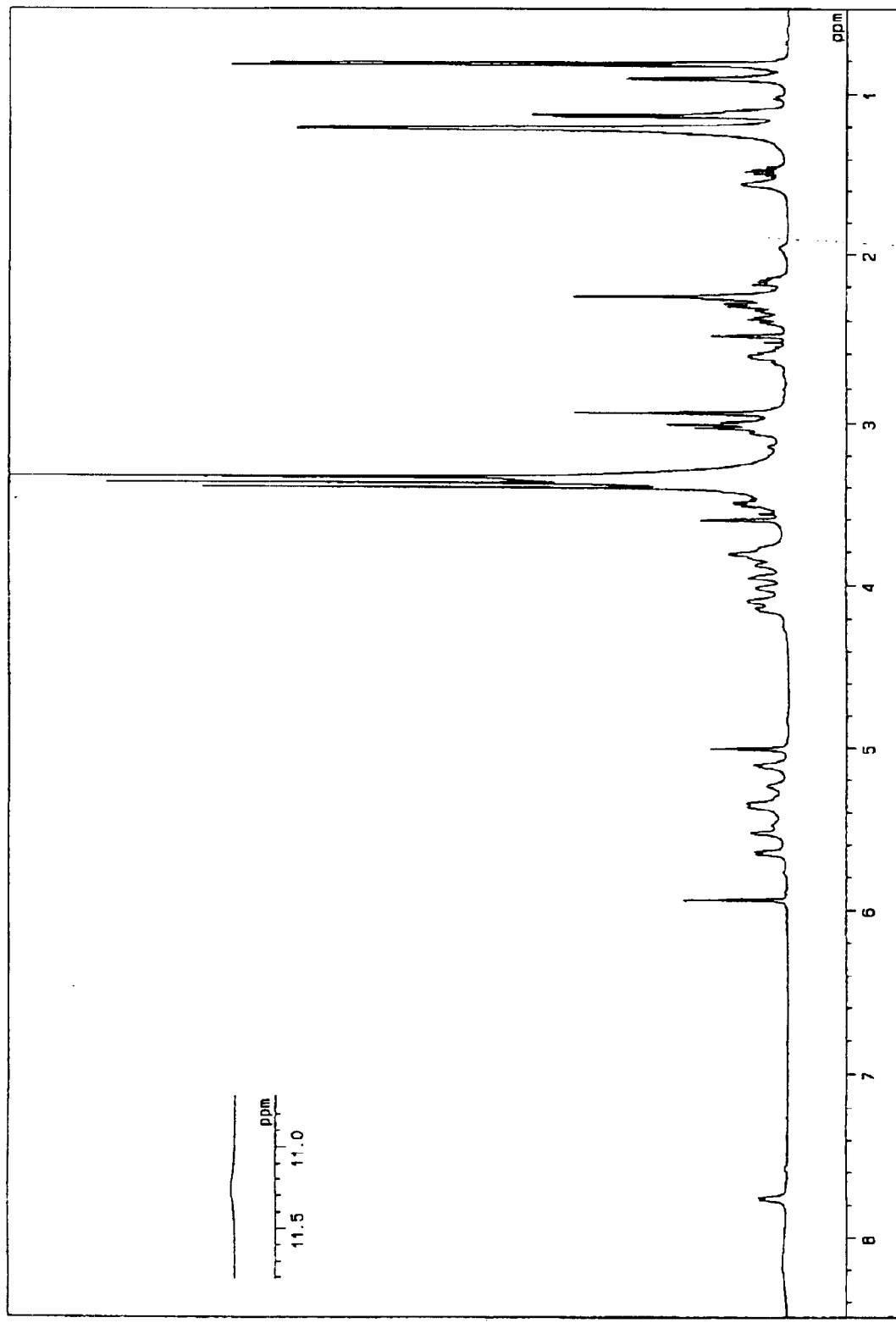
FIG. 19 is proton nuclear magnetic resonance spectrum of caprazamycin F as measured in DMSO-$d_6$ solution at 500 MHz at room temperature.
Figure 20:
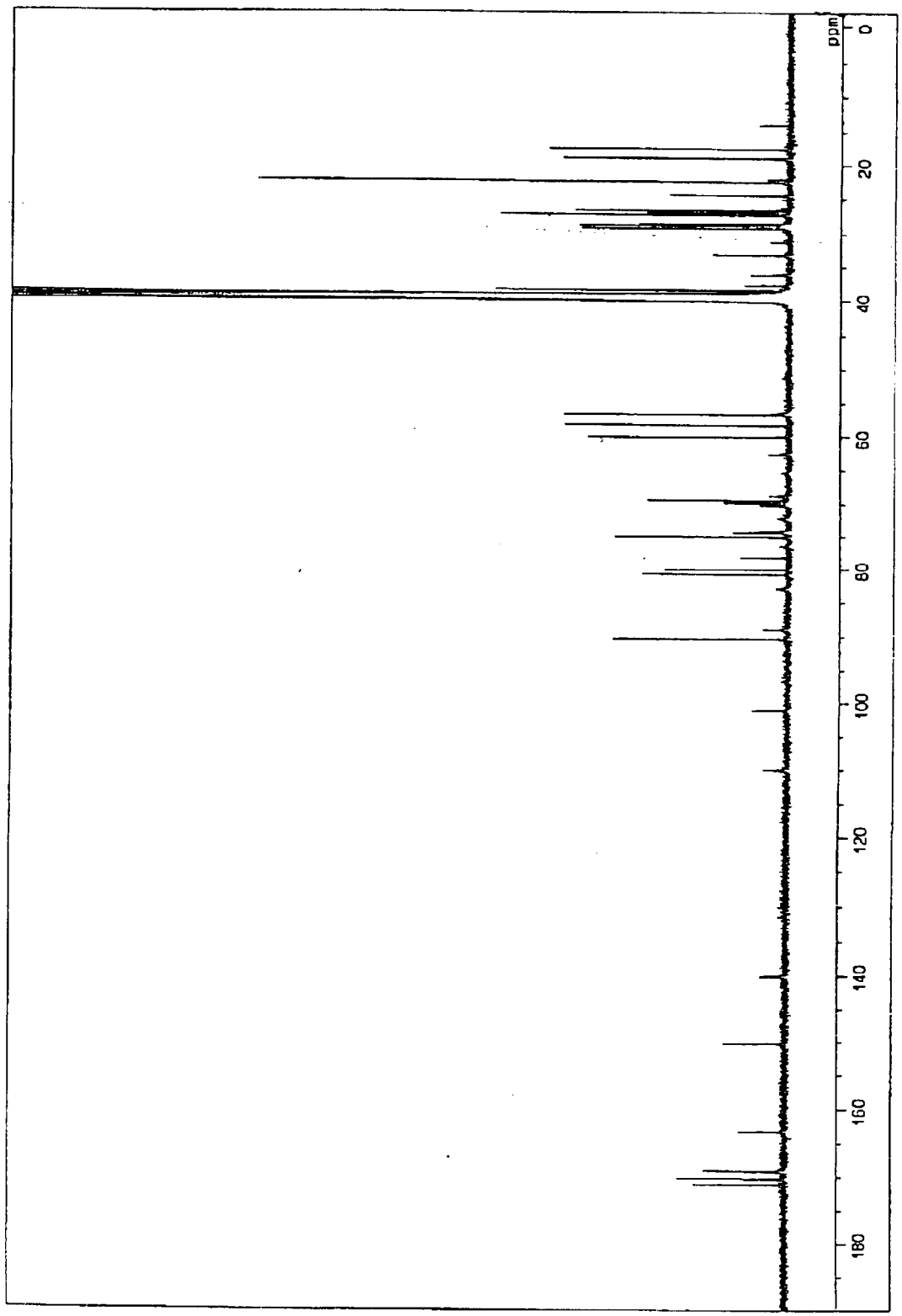
FIG. 20 is $^{13}$C-nuclear magnetic resonance spectrum of caprazamycin F as measured in DMSO-$d_6$ solution at 125 MHz at room temperature.

This invention is now illustrated in more detail with reference to the following Examples.

EXAMPLE 1

Production of the antibiotic caprazamycins A, B, C, E and F

Streptomyces sp. MK730-62F2 (deposited under the depository number of FERM BP-7218), which had been cultured on agar slant culture medium, was inoculated in a culture medium. The culture medium used here had been prepared by placing into Erlenmeyer flasks (of 500 ml-capacity) 110 ml-portions of a liquid culture medium comprising 2% galactose, 2% dextrin, 1% glycerine, 1% Bacto-soyton (a product of Difco Co.), 0.5% corn steep liquor, 0.2% ammonium sulfate, and 0.2% calcium carbonate (adjusted a pH of 7.4) and sterilizing the culture medium in the flasks at 120° C. for 20 minutes in a usual manner, before the inoculation of the strain MK730-62F2 was done. The liquid culture medium so inoculated was then subjected to shaking cultivation with rotation at 30° C. for 2 days, thereby to afford a seed culture broth as intended.

In a tank fermenter (of 30 L-capacity), there was prepared 15 liters of a culture medium comprising 2.4% tomato paste (a product of Kagome Co.), 2.4% dextrin, 1.2% yeast extract (a product of Oriental Co.) and 0.0006% cobalt chloride (adjusted to a pH of 7.4), which was then sterilized so as to afford the productive culture medium. To this productive culture medium was inoculated a 2% proportion of the above-mentioned seed culture broth. The cultivation of the strain MK730-62F2 was conducted in the tank fermenter under the conditions that the cultivation was effected for 6 days at a temperature of 27° C. with aeration of 15 L of air per minute and agitation at 200 rpm.

The resulting culture broth was centrifuged to separate into the culture broth filtrate (12 L) and the cultured microbial cells. Subsequently, methanol (6 L) was added to the microbial cells so separated, and the resultant mixture was well stirred to extract the caprazamycins from the cells into methanol. The culture broth filtrate as obtained and the methanolic extract of the cells (the methanol extract) were combined together, and the resulting mixture (18 L) was passed through a column comprising 750 ml of a synthetic adsorbent resin made of aromatic polymer, namely "Diaion HP-20" resin (a product of Mitsubishi Chemical Co., Japan), whereby the caprazamycins were adsorbed in the Diaion HP-20 resin. Through this Diaion HP-20 resin column containing the adsorbed caprazamycins, were passed a volume of deionized water, 50% aqueous methanol (a mixture of 50% methanol and 50% water), 80% aqueous methanol (a mixture of 80% methanol and 20% water), 80% aqueous acetone (a mixture of 80% acetone and 20% water) and acetone (each 2.25 L), in order. The caprazamycins have been eluted out mainly in the eluate fraction which was obtained by eluting with the 80% aqueous acetone. In addition, the eluate fraction as eluted with the 50% aqueous methanol and the eluate fraction as eluted with the 80% aqueous methanol have contained caprazamycins, too. These two eluate fractions containing caprazamycins as eluted with the 50% aqueous methanol and with the 80% agulous methanol were combined together. The resulting mixture of these eluate fractions was again passed through a column of Diaion HP-20 resin (750 ml), whereby caprazamycins were adsorbed in the adsorbent resin of this column. Thereafter, 80% aqueous methanol (2.25 L) was passed through this column. Then, elution was effected by passing 80% aqueous acetone (2.25 L) through the column. The resulting eluate as eluted with the 80% aqueous acetone at this time was then combined with the first-mentioned eluate fraction which had been obtained by eluting with the 80% aqueous acetone at the earlier stage. The resulting mixture was concentrated to dryness under a reduced pressure, whereby a partially purified product comprising caprazamycins (10.1 g) was obtained.

This partially purified product comprising caprazamycins (10.1 g) was then dissolved in a mixed solvent (50 ml) of chloroform-methanol (=1:2), and the resulting solution was added with Kieselgur (Art. 10601, a product of Merck & Co.,) (50 ml) and the solvent was evaporated off to dryness under a reduced pressure. The resulting Kieselgur solids containing caprazamycins adsorbed therein was placed on the top of a silica gel column (54 mm inner diameter×200 mm height) to be subjected to a chromatography. The development solvents used for this chromatography purpose were solvent mixtures of chloroform-methanol-water (=4:1:0.1); chloroform-methanol-water (=2:1:0.2); and chloroform-methanol-water (=1:1:0.2), and 1.35 L of the solvent mixture was used for each time. The developing operations were carried out in order, with these solvent mixtures. The eluates from the silica gel column were collected each in fractions by means of a fraction collector, so that fractions Nos. 1 to 53 were collected each in 20 g-portions, and so that fractions Nos. 54 to 117 were collected each in 19 g-portions. In this way, the active fractions containing caprazamycins were eluted in fractions Nos. 66 to 83. These active fractions Nos. 66 to 83 were combined together and then concentrated to dryness under a reduced pressure, thus to afford a partially purified product comprising caprazamycins (625.3 mg).

Methanol (5 ml) was added to the partially purified product (625.3 mg) thus obtained. The resulting solution was allowed to stand at 5° C. under cold and dark conditions, whereby a fraction of precipitate as deposited (537.3 mg) was obtained as a product which comprised caprazamycins.

Subsequently, the deposited precipitate (537.3 mg) comprising caprazamycins was purified by subjecting it to HPLC (CAPCELL PAX C18, diameter 20 mm×height 250 mm, a product of Shiseido Co., Japan). In this HPLC, the development was conducted with 50% acetonitrile-water-0.05% formic acid as the development solvent (at a flow rate of 12.0 ml/min.), whereby caprazamycin A was eluted after 61 to 68 minutes; caprazamycin B was eluted after 52 to 60 minutes; caprazamycin C was eluted after 39 to 41 minutes; caprazamycin E was eluted after 25 to 28 minutes; and caprazamycin F was eluted after 22 to 25 minutes of the development. These active fractions were collected separately for each of the desired caprazamycins. Each of the separately collected active fractions was concentrated to dryness under a reduced pressure, to afford caprazamycin A (56.9 mg), caprazamycin B (90.3 mg), caprazamycin C (19.7 mg), caprazamycin E (30.3 mg) and caprazamycin F (25.5 mg), respectively.

INDUSTRIAL APPLICABILITY

As described hereinbefore, caprazamycins A, B, C, E and F having the general formula (I), which are provided as novel antibiotics according to this invention, each have excellent antibacterial activities against various acid-fast bacteria and various bacteria as well as their drug-resistant strains. Therefore, a caprazamycin according to this invention is effective and useful for treating bacterial infections as caused by acid-fast bacteria or bacteria.

What is claimed is:

1. An antibiotic, caprazamycin A, caprazamycin B, caprazamycin C, caprazamycin E or caprazamycin F, which is a compound represented by the following formula (I)

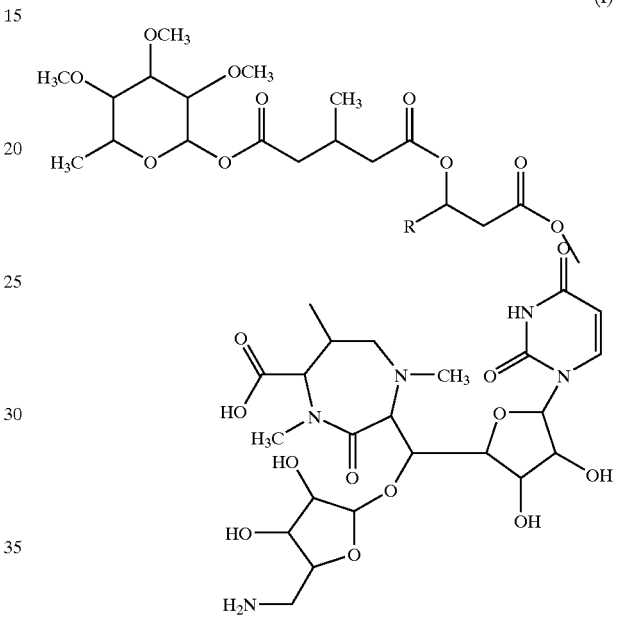

(I)

wherein, R is tridecyl group for caprazamycin A; 11-methyl-dodecyl group for caprazamycin B; dodecyl group for caprazamycin C; undecyl group for caprazamycin E; and 9-methyl-decyl group for caprazamycin F, or a pharmaceutically acceptable salt thereof.

2. The antibiotic of claim 1 which is caprazamycin A represented by the following formula (Ia)

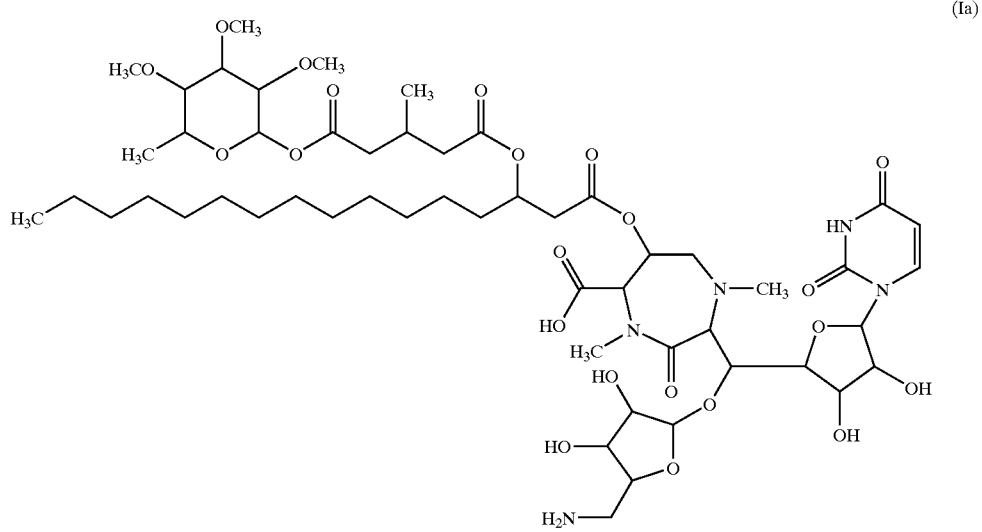

(Ia)

that is, the compound of formula (I) shown in claim 1 where R is tridecyl group —(CH$_2$)$_{12}$—CH$_3$.

3. The antibiotic of claim 1 which is caprazamycin B represented by the following formula (Ib)

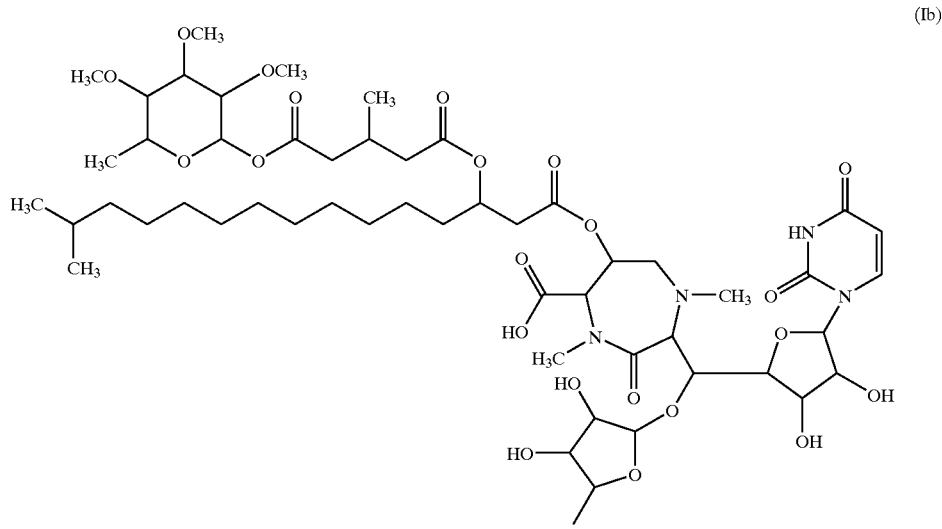

(Ib)

that is, the compound of formula (I) shown in claim 1 where R is 11-methyl-dodecyl group

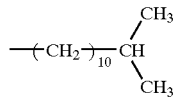

4. The antibiotic of claim 1 which is caprazamycin C represented by the following formula (Ic)

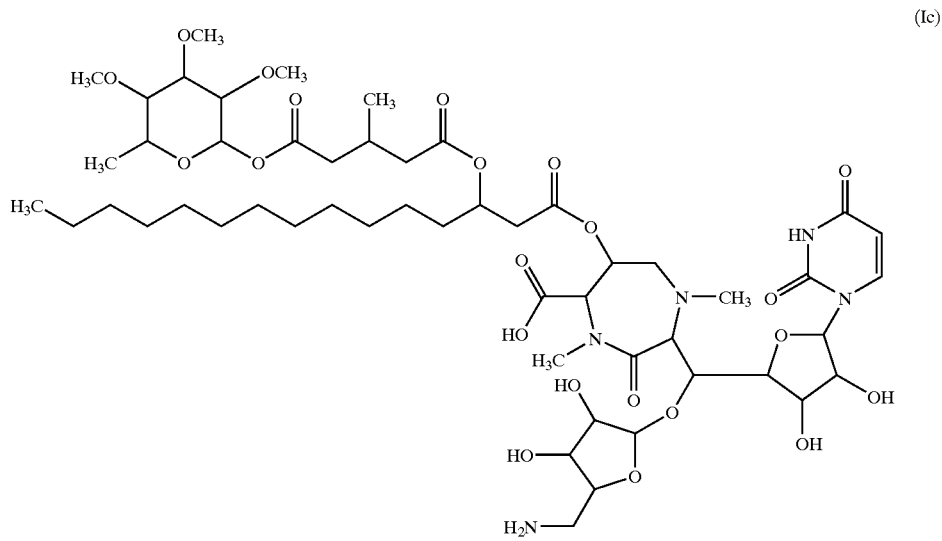

(Ic)

that is, the compound of formula (I) shown in claim 1 where R is dodecyl group —(CH$_2$)$_{11}$—CH$_3$.

5. The antibiotic of claim 1 which is caprazamycin E represented by the following formula (Ie)

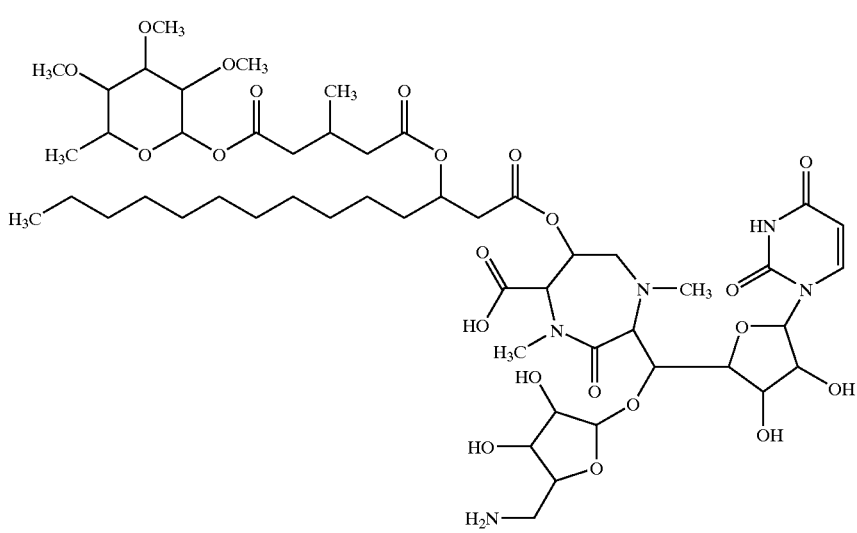

(Ie)

that is, the compound of general formula (I) shown in claim 1 where R is undecyl group —(CH$_2$)$_{10}$—CH$_3$.

6. The antibiotic of claim 1 which is caprazamycin F represented by the following formula (If)

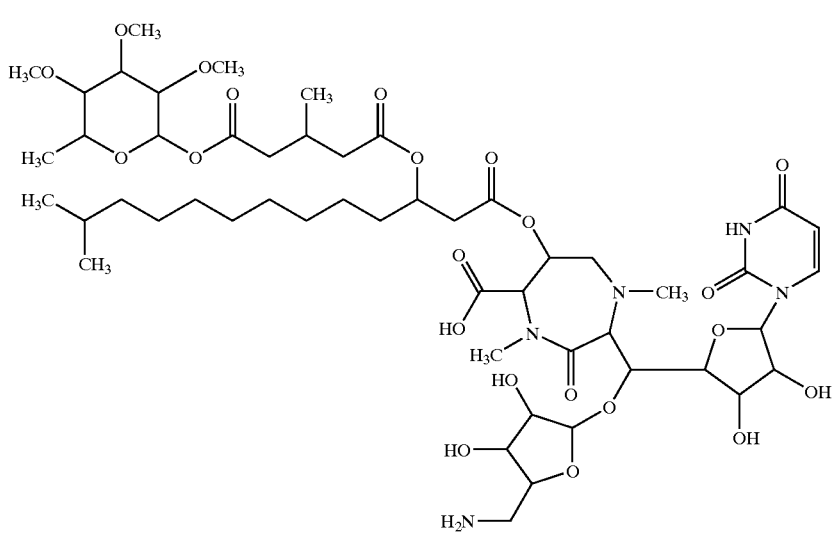

(If)

that is, the compound of formula (I) shown in claim 1 where R is 9-methyl-decyl group

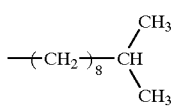

7. A process for the production of an antibiotic represented by formula (I) in claim 1, the process comprising culturing the microbial strain Streptomyces sp. MK730-62F2 which is capable of producing at least one of caprazamycin A, caprazamycin B, caprazamycin C, caprazamycin E and caprazamycin F, and recovering at least one of caprazamycin A, B, C, E and F from the resulting culture.

8. A pharmaceutical composition having as an active ingredient at least one of caprazamycin A, B, C, E and F having the formula (I) given in claim 1, or a salt thereof, in admixture with a pharmaceutically acceptable carrier or carriers.

9. The composition of claim 8 which is an antibacterial.

10. A biologically pure culture of Streptomyces sp. MK730-62F2 which has a characteristic nature that it is capable of producing caprazamycin A, B, C, E and F of the formula (I) given in claim 1.

* * * * *